US010266839B2

(12) United States Patent
Park et al.

(10) Patent No.: US 10,266,839 B2
(45) Date of Patent: Apr. 23, 2019

(54) METHOD FOR INACTIVATING TARGET TRANSCRIPTION FACTOR USING ARTIFICIAL SMALL INTERFERING PEPTIDE AND USE THEREOF

(71) Applicant: SNU R&DB Foundation, Seoul (KR)

(72) Inventors: Chung Mo Park, Gyeonggi-do (KR); Pil Joon Seo, Jeollabuk-do (KR)

(73) Assignee: SNU R&DB FOUNDATION, Seoul (KR)

( * ) Notice: Subject to any disclaimer, the term of this patent is extended or adjusted under 35 U.S.C. 154(b) by 468 days.

(21) Appl. No.: 14/772,306

(22) PCT Filed: Dec. 20, 2012

(86) PCT No.: PCT/KR2012/011121
§ 371 (c)(1),
(2) Date: Jan. 7, 2016

(87) PCT Pub. No.: WO2014/073742
PCT Pub. Date: May 15, 2014

(65) Prior Publication Data
US 2016/0138036 A1 May 19, 2016

(30) Foreign Application Priority Data

Nov. 7, 2012 (KR) .................. 10-2012-0125115

(51) Int. Cl.
*C12N 15/82* (2006.01)
*C07K 2/00* (2006.01)
*C07K 14/415* (2006.01)

(52) U.S. Cl.
CPC ............ *C12N 15/8261* (2013.01); *C07K 2/00* (2013.01); *C07K 14/415* (2013.01); *C12N 15/827* (2013.01); *C12N 15/8216* (2013.01); *C12N 15/8217* (2013.01); *C12N 15/8266* (2013.01)

(58) Field of Classification Search
None
See application file for complete search history.

(56) References Cited

U.S. PATENT DOCUMENTS

| | | | | |
|---|---|---|---|---|
| 6,653,527 | B1 * | 11/2003 | Deng ................... | C07K 14/415 435/252.3 |
| 7,692,065 | B2 | 4/2010 | Harper et al. | |
| 7,956,242 | B2 * | 6/2011 | Zhang .................. | C07K 14/415 800/295 |
| 7,960,612 | B2 * | 6/2011 | Zhang .................. | C07K 14/415 800/298 |
| 2009/0049566 | A1 * | 2/2009 | Zhang .................. | C07K 14/415 800/266 |

FOREIGN PATENT DOCUMENTS

KR 10-2007-0076918 A 7/2007
KR 20-1200-17913 A 2/2012

OTHER PUBLICATIONS

Seo et al (2012, The Plant Journal 72:162-172).*
Siegfried et al (1999, Development 126:4117-4128).*
Krizek et al (1996, "Mapping the Protein Regions Responsible for the Functional Specificities of the *Arabidopsis* MADS Domain Organ-Identity Proteins", PNAS 93:4063-4070).*
International Search Report for PCT/KR2012/011121.
Seo, Pil Joon et al., "Competitive inhibition of transcription factors by small interfering peptides" Trends in Plant Science, Oct. 2011, vol. 16, No. 10, pp. 541-549.
Pil Joon Sea, A Self-Regulatory Circuit of Circadian Clock-Associated1 Underlies the Circadian Clock Regulation of Temperature Responses in *Arabidopsis*, The Plant Cell, vol. 24: 2427-2442, Jun. 2012.
Pil Joon Sea et al, Two splice variants of the IDD14 transcription factor competitively form nonfunctional heterodimers which may regulate starch metabolism, Nature Communications, 2:303, DOI: 10.1038/ncomms1303.
Shin-Young Hong et al., Nuclear Import and DNA Binding of the ZHD5 Transcription Factor Is Modulated by a Competitive Peptide Inhibitor in Arabidopsis, Journal of Biological Chemistry, vol. 286, No. 2, Jan. 14, 2011.
Jose M Polo1 et al., Specific peptide interference reveals BCL6 transcriptional and oncogenic mechanisms in B-cell lymphoma cells, Nature Medicine, vol. 10, No. 12, Dec. 2004, pp. 1329-1335.
Yoshibumi Komeda, Genetic Regulation of Time to Flower in *Arabidopsis thaliana*, Annual Review. Plant Biol. 2004. 55:521-35.
Robert Schaffer et al., The late elongated hypocotyl Mutation of *Arabidopsis* Disrupts Circadian Rhythms and the Photoperiodic Control of Flowering, Cell, vol. 93, pp. 1219-1229, Jun. 26, 1998.
So-Dam Yang et al., The *Arabidopsis* NAC Transcription Factor VNI2 Integrates Abscisic Acid Signals into Leaf Senescence via the COR/RD Genes, The Plant Cell, vol. 23: 2155-2168, Jun. 2011.
Jihyun Moon et al., The SOC1MADS-box gene intergrates vernalization and gibberellin signals for flowering in Arabifopsis, The Plant Journal (2003) 35, pp. 613-623.
Friedrich-Schiller-Universität Jena et al., MIKC-type MADS-domain proteins: structural modularity, protein interactions and network evolution in land plants, Gene, 347 (2005), pp. 183-198.

(Continued)

*Primary Examiner* — Stuart F Baum
(74) *Attorney, Agent, or Firm* — The PL Law Group, PLLC

(57) ABSTRACT

The present invention relates to a method for targeted inactivation of transcription factor using an artificial small interfering peptide and a use thereof. According to the present invention, an artificial small interfering peptide (a-siPEP) as a truncated from of the transcription factor for regulating transcription by dimerization was produced. It was also confirmed that, as a-siPEP forms a heterodimer with a transcription factor, DNA binding and transport into a nucleus of the transcription factor are inhibited, so that inactivation of the transcription factor is achieved at protein level. The method for inhibiting transcription factor activity using a-siPEP can replace a gene knock-out method and it allows protein-level inhibition of a transcription factor. Also, it is a transcription regulation method with high precision and high efficiency that can be applied for both monocot and dicot plants.

10 Claims, 8 Drawing Sheets

Specification includes a Sequence Listing.

(56) References Cited

OTHER PUBLICATIONS

Steven J. Clough et al., Floral dip: a simplified method for Agrobacterium-mediated transformation of *Arabidopsis thaliana*, The Plant Journal, (1998) 16(6), pp. 735-743.
John Vogel et al., High-efficiency Agrobacterium-mediated transformation of Brachypodium distachyon inbred line Bd21-3, Plant Cell Rep, (2008) 27: pp. 471-478.
Michael K. Udvardi et al., Eleven Golden Rules of Quantitative RT-PCR, The Plant Cell, vol. 20, pp. 1736-1737, Jul. 2008.
Sang-Dong Yoo et al., *Arabidopsis mesophyll* protoplasts: a versatile cell system for transient gene expression analysis, Nature Protocols, vol. 2, No. 7, 2007, pp. 1565-1572.
Richard G. H. Immink et al., Analysis of MADS box protein—protein interactions in living plant cells, PNAS, Feb. 19, 2002, vol. 99, No. 4, pp. 2416-2421.
Kian-Hong Ng et al., Agamous Controls Giant Killer, a Multifunctional Chromatin Modifier in Reproductive Organ Patterning and Differentiation, PLoS Biology, Nov. 2009, vol. 7, Issue 11, e1000251.
Tsuyoshi Mizoguchi et al., LHY and CCA1 Are Partially Redundant Genes Required to Maintain Circadian Rhythms in *Arabidopsis*, Developmental Cell, vol. 2, pp. 629-641, May 2002.
Sheen X. Lu et al., Circadian Clock Associated1 and Late Elongated Hypocotyl Function Synergistically in the Circadian Clock of *Arabidopsis*, Plant Physiology, Jun. 2009, vol. 150, pp. 834-843.
F. A. Krens et al., In vitro transformation of plant protoplasts with Ti-plasmid DNA, Nature, vol. 296, No. 4, pp. 72-74, Mar. 1982.
I. Negrutiu et al, Hybrid genes in the analysis of transformation conditions, Plant Molecular Biology, 8: pp. 363-373, (1987).
R. D. Shillito et al., High Efficiency Direct Gene Transfer to Plants, Bio/Technology, vol. 3, Dec. 1985, pp. 1099-1103.
Ann Crossway et al., Intergration of foreign DNA following microinjection of tobacco mesophyll protoplasts, Mol Gen Genet, 1986, 202: pp. 179-185.
T. M. Klein et al., High-velocity microprojectiles for delivering nucleic acids into living cells, Nature, vol. 327, No. 7, pp. 70-73, May 1987.
Targeted inactivation of transcription factors by overexpression of their truncated forms in plants, The Plant Journal, (2012) 72, pp. 162-172.
Ju Yun et al., Small interfering peptides as a novel way of transcriptional control, Plant Signaling & Behavior, 3:9, pp. 615-617, Sep. 2008.
Seo, Pil Joon et al., "Targeted inactivation of transcription factors by overexpression of their truncated forms in plants" The Plant Journal, Oct. 2012, vol. 72, No. 1, pp. 162-172.
Yun, Ju et al., "Small interfering peptides as a novel way of transcriptional control" Plant signaling & behavior, Sep. 2008, vol. 3, No. 9, pp. 615-617.

* cited by examiner

METHOD FOR INACTIVATING TARGET TRANSCRIPTION FACTOR USING ARTIFICIAL SMALL INTERFERING PEPTIDE AND USE THEREOF

CROSS REFERENCE TO RELATED APPLICATIONS

This application is a National Phase application under 35 U.S.C. § 371 of International Application No. PCT/KR2012/011121, filed Dec. 20, 2012, which claims priority to and the benefit of Republic of Korea Patent Application Nos. 10-2012-0125115 filed Nov. 7, 2012, the disclosures of which are incorporated herein by reference in its entirety.

TECHNICAL FIELD

The present invention relates to a method for targeted inactivation of transcription factor using an artificial small interfering peptide and a use thereof. More specifically, it relates to an artificial small interfering peptide (a-siPEP) characterized by comprising essentially a dimerization domain of a plant transcription factor and being a truncated form of the transcription factor, a gene encoding the artificial small interfering peptide, a recombinant plant vector comprising the gene, a plant transformed with the recombinant plant vector to inhibit transcription factor activity, a method for inhibiting transcription factor activity of a plant by using the artificial small interfering peptide, a method for producing a transgenic plant with inhibited transcription factor activity by using the aforementioned the artificial small interfering peptide, a transgenic plant having inhibited transcription factor activity which is produced by the aforementioned method and a seed thereof, and a composition for inhibiting transcription factor activity of a plant which comprises a recombinant vector comprising a gene encoding the artificial small interfering peptide.

BACKGROUND ART

Targeted manipulation of gene expression is a fundamental concern in crop biotechnology. A variety of molecular methods has been developed to manipulate gene expression. However, targeted gene inactivation is still practically difficult in most crop species. RNA interference (RNAi), which is frequently used for targeted gene silencing, often suffers from off-target effects and unstable gene suppression. Engineered nuclease-based tools, such as zinc-finger nucleases (ZFNs) and transcription activator-like effector nucleases (TALENs), have been developed to induce site-specific genome modifications. These approaches facilitate precise genetic modifications but require much time and labor for extensive screening.

It has recently been reported that the activities of dimeric transcription factors are efficiently suppressed by genome-encoded siPEPs that competitively form nonfunctional heterodimers in plants (Seo et al., Trends Plant Sci. 16, 541-549, 2011). The LITTLE ZIPPER (ZPR) proteins consisting of 67-105 residues contain leucine zipper motifs and interact with class III homeodomain-leucine zipper (HD-ZIP III) transcription factors. However, they lack protein domains required for DNA binding and transcriptional activation. As a result, the ZPR proteins attenuate the HD-ZIPIII transcription factor activities by reducing DNA binding affinity and transcriptional regulation activity. Similarly, the MINI FINGER (MIF) proteins interfere with zinc finger-homeodomain (ZHD) transcription factors, which function in multiple hormone signalings and floral development, by inhibiting nuclear import and DNA binding of the target transcription factors (Hong et al., J. Biol. Chem. 286, 1659-1668, 2011).

Notably, the siPEPs are also produced by alternative splicing of transcription factor genes. The Arabidopsis INDETERMINATE DOMAIN 14 (IDD14) gene undergoes alternative splicing, producing two spliced isoforms, designated IDD14α and IDD14β. The IDD14β form has disrupted DNA-binding domain but is able to form heterodimers with the IDD14α □ form (Seo et al., Nat. Commun. 2, 303, 2011b), further extending the repertoire of the siPEP in plants.

In animals, a variety of cancers are caused by constitutive expression of transcription factor genes. It has been shown that synthetic peptides, when injected into animal tissues, efficiently repress the activities of oncogenic transcription factors (Polo et al., Nat. Med. 10, 1329-1335, 2004). In addition, dynamic dimer formation of transcription factors, such as STAT3 (signal transducers and activators of transcription 3), c-Myc, Max, c-Jun, and c-Fos, is disturbed by peptidomimetics, small protein-like molecules that structurally mimic protein domains required for dimerization. The small molecules suppress transcription factor activities by inhibiting either protein-protein interactions or DNA binding, similar to what have been observed with genomic siPEPs in plants.

Inventors of the present invention explored the biotechnological relevance of engineered transcription factor proteins, which designated artificial siPEPs (a-siPEPs) because of their structural mimicry to genomic siPEPs in plants. Gene sequences encoding potential a-siPEPs of SOC1 and AG MADS box transcription factors, which function in flowering induction and floral organogenesis, respectively (Komeda, Annu. Rev. Plant Biol. 55, 521-535, 2004), and the LHY MYB transcription factor involved in circadian clock control (Schaffer et al., Cell, 93, 1219-1229, 1998) were transformed into Arabidopsis and Brachypodium. Phenotypic comparison and biochemical and molecular analyses revealed that the a-siPEPs inhibit nuclear import and DNA binding by forming nonfunctional dimers in both plant species, supporting that the a-siPEP tool could be employed to inactivate specific transcription factors in crop plants.

Meanwhile, in Korean Patent Application Publication No. 2012-0017913, "Inhibitor of transcription factor having fusion protein which contains DNA binding domain and protein transport domain of transcription factor and preparation method thereof" is disclosed. Further, in Korean Patent Application Publication No. 2007-0076918, "Plants enhanced by the development of wide-leafed, late-flowering and environmental stress-resistant by transforming the transcription factor gene AtMYB44" is disclosed. However, the method for targeted inactivation of transcription factor using an artificial small interfering peptide and uses thereof that are described in the present invention have never been disclosed in any of those literatures.

SUMMARY

The present invention is devised in view of the aforementioned needs. Inventors of the present invention produce a plant expressing an artificial small interfering peptide (a-siPEP) gene, which is a truncated form of a transcription factor for regulating transcription according to dimerization. It was further confirmed by the inventors of the present invention that, as a-siPEP forms a heterodimer with a transcription factor, DNA binding and transport into a nucleus of the transcription factor are inhibited, so that inactivation of the transcription factor is achieved at protein level in a dicot plant and a monocot plant. The present invention is completed accordingly.

To solve the problems described above, the present invention provides an artificial small interfering peptide (a-siPEP) characterized by comprising essentially a dimerization domain of a plant transcription factor and being a truncated form of the transcription factor.

The present invention further provides a gene encoding the artificial small interfering peptide.

The present invention further provides a recombinant plant vector comprising the gene.

The present invention further provides a plant transformed with the recombinant plant vector to inhibit transcription factor activity.

The present invention further provides a method for inhibiting transcription factor activity of a plant comprising transforming a plant cell with the recombinant vector comprising the gene encoding the artificial small interfering peptide to overexpress the gene encoding the artificial small interfering peptide.

The present invention further provides a method for producing a transgenic plant with inhibited transcription factor activity comprising transforming a plant cell with the recombinant vector comprising the gene encoding the artificial small interfering peptide to overexpress the gene encoding the artificial small interfering peptide.

The present invention further provides a transgenic plant having inhibited transcription factor activity which is produced by the aforementioned method, and a seed thereof.

The present invention still further provides a composition for inhibiting transcription factor activity of a plant which comprises a recombinant vector comprising a gene encoding the artificial small interfering peptide.

According to the present invention, a method for inhibiting transcription factor activity based on overexpression of the artificial small interfering peptide siPEP (a-siPEP) gene allows protein-level inhibition of a transcription factor and it can replace a gene knock-out method. As the method can be applied for both monocot and dicot plants and has high precision and efficiency, it can contribute to advancement of agricultural and plant seed industry in accordance with development of crops with improved traits using a-siPEP.

(a) *Brachypodium* SOC1 constructs used. Numbers indicate residue positions. Arrowheads and bold bars indicate the positions of BdSOC1 and BdS-K primers used to detect BdSOC1 and BdS-K transcripts, respectively. aa, amino acid.

(b and c) Phenotypes and flowering of *Brachypodium* plants overexpressing BdSOC1 genes. Eight-week-old plants grown in soil were photographed (b). White arrowheads indicate headings. Flowering times were measured by counting days at heading emergence (c). Twenty plants were averaged and statistically treated. Different letters represent significant difference at $P<0.05$ (one-way ANOVA with Fisher's post hoc test).

(d) Expression of BdSOC1 and its downstream genes. mRNA levels of genes acting downstream of BdSOC1, such as BdAP1, BdCAL, BdFUL, BdLFY, and BdSPL8, and encoding the BdS-K domain (BdS-K) were examined by qRT-PCR. Biological triplicates were averaged and statistically treated using a Student's t-test (*$P<0.01$). Bars indicate standard error of the mean.

Figure 6:
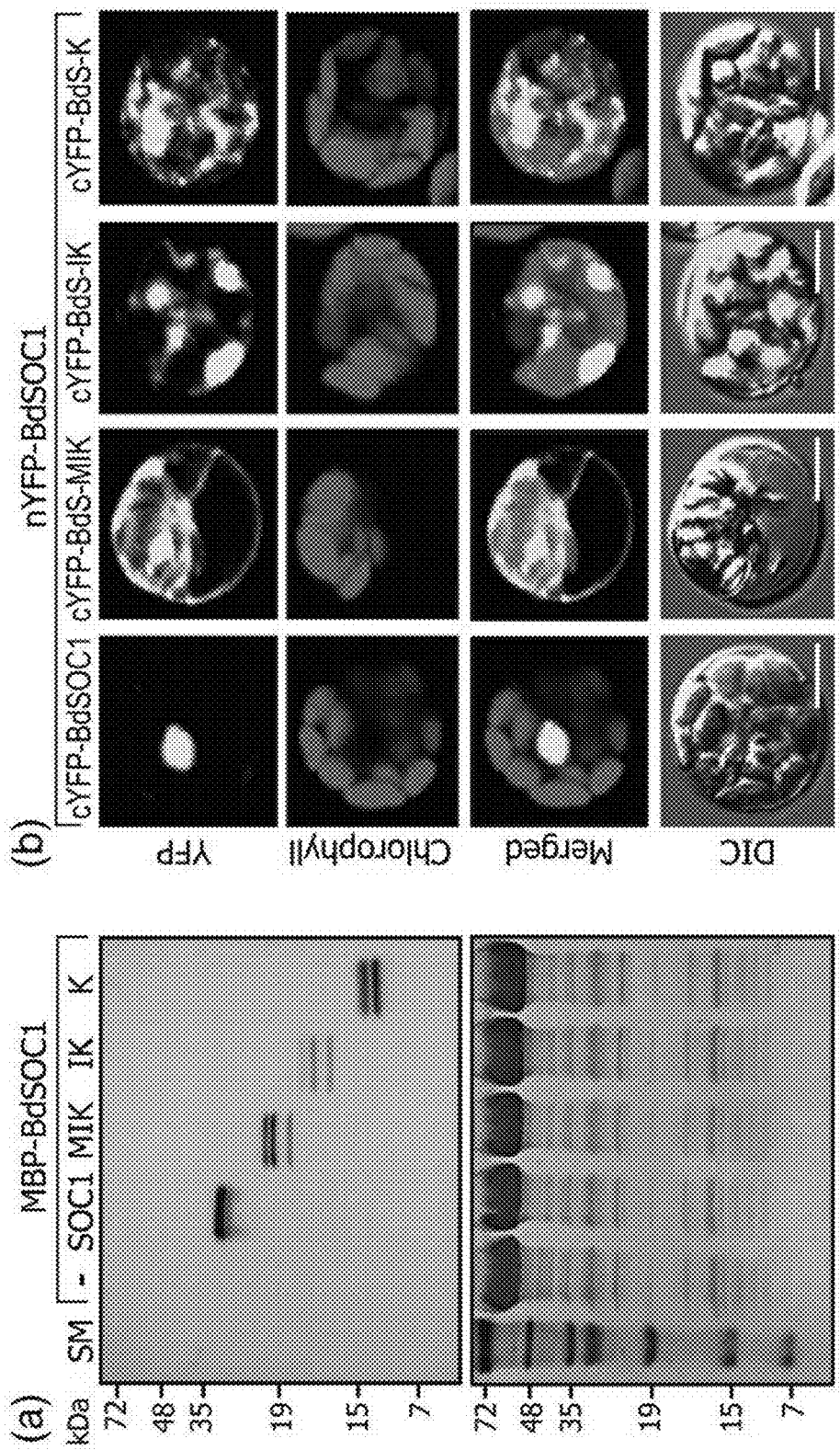

FIG. 6 shows attenuation of BdSOC1 nuclear localization by a-siPEP.

(a) in vitro pull-down assays. The BdSOC1 protein was prepared as recombinant BdSOC1-MBP fusion in *E. coli* cells. The $^{35}$S-labeled BdSOC1 polypeptides were prepared by in vitro translation. Part of Coomassie-stained gel is shown (bottom panel).

(b) BiFC assays. Partial YFP fusion constructs were transiently expressed in *Brachypodium* protoplasts. Scale bars=10 µm.

Figure 7:
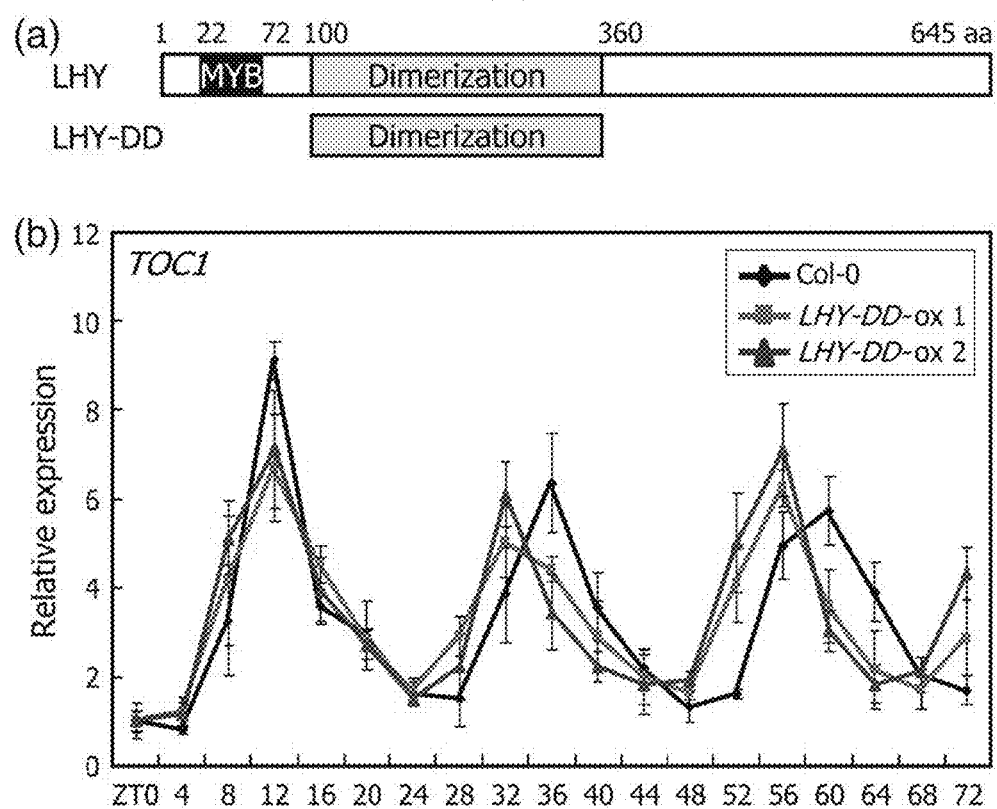

FIG. 7 shows a-siPEP-mediated inhibition of LHY activity in circadian clock control.

(a) Domain structures of LHY proteins. Numbers indicate residue positions. DD, dimerization domain. aa, amino acid.

(b) Circadian trace of TOC1 gene expression in LHY-DD-ox transgenic plants. Plants grown on MS-agar plates under neutral day cycles (12-h light and 12-h dark) for 10 days were transferred to continuous light conditions. Two independent LHY-DD-ox transgenic lines were included in the assays. Whole plants were harvested at zeitgeber time (ZT) points up to 72 h, and gene transcript levels were determined by qRT-PCR. Biological triplicates were averaged. Bars indicate standard error of the mean.

Figure 8:
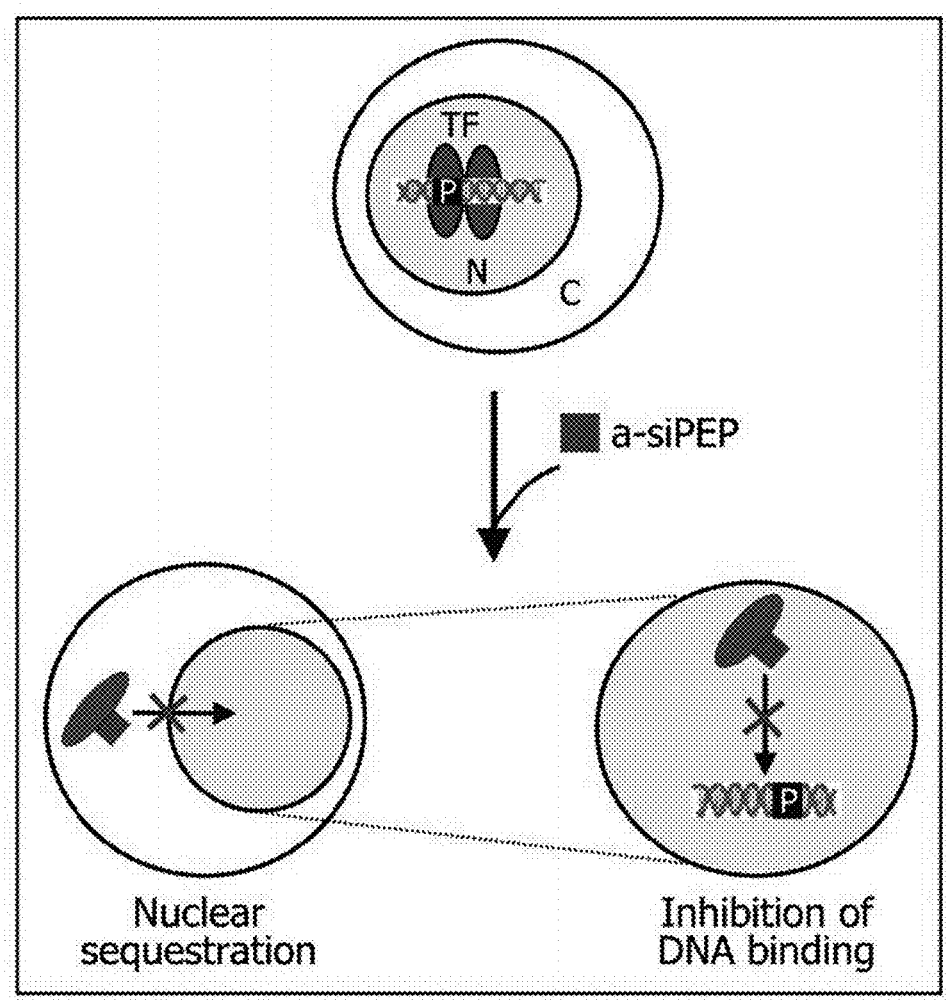

FIG. 8 shows working model of a-siPEPs. a-siPEP forms nonfunctional heterodimer with target transcription factor (TF), resulting in sequestration from the nucleus (N) and/or inhibition of DNA binding. P, promoter. C, cytoplasm.

DETAILED DESCRIPTION

In order to achieve the object of the present invention, the present invention provides an artificial small interfering peptide (a-siPEP) characterized by comprising essentially a dimerization domain of a plant transcription factor and being a truncated form of the transcription factor.

According to one embodiment of the present invention, the transcription factor may regulate the transcription based on dimerization. Preferably, it may regulate the transcription based on forming of a homodimer or a heterodimer. Most preferably, it may regulate the transcription based on forming of a homodimer, but it is not limited thereto.

According to one embodiment of the present invention, the artificial small interfering peptide can regulate transcription factor activity, and preferably inhibit the transcription factor activity, by forming a nonfunctional dimer with a transcription factor, but it is not limited thereto.

According to one embodiment of the present invention, the artificial small interfering peptide can regulate the transcription factor activity, and preferably inhibit the transcription factor activity, by inhibiting DNA binding or transport of a transcription factor to a nucleus according to forming of a nonfunctional dimer with a transcription factor, as shown in FIG. 8, but it is not limited thereto.

When the inhibition of transcription factor activity by the artificial small interfering peptide of the present invention is explained in detail, it is noted that the artificial small interfering peptide of the present invention consists of a part of a plant transcription factor (i.e., truncated from) comprising essentially a dimerization domain of a plant transcription factor, which regulates the transcription based on dimerization. The artificial small interfering peptide forms, upon binding with a normal transcription factor produced from a plant, a nonfunctional dimer, and the binding between normal transcription factors can be competitively inhibited according to above process. In addition, the nonfunctional dimer has inhibited DNA binding or inhibited transport to nucleus. Thus, according to inhibited dimerization of normal transcription factors and forming of a nonfunctional dimer, the activity of the transcription factor is inhibited, and as a result, the transcription regulated by the transcription factor can be inhibited.

According to one embodiment of the present invention, the transcription factor may contain a DNA binding domain, a dimerization domain (i.e., domain for mediating protein-protein interaction), a transcription factor-homodimer formation contribution domain, and a transcription regulation domain, and it preferably contains a DNA binding domain and a dimerization domain (i.e., domain for mediating protein-protein interaction), but the present invention is not limited thereto. Thus, the artificial small interfering peptide of the present invention may be a truncated form of a transcription factor which contains, for inhibiting the transcription factor activity, only a dimerization domain, a truncated form of a transcription factor which contains, for inhibiting the transcription factor activity, a dimerization domain and a DNA binding domain but not a transcription regulation domain, or a truncated form of a transcription factor which contains, for inhibiting the transcription factor activity, a dimerization domain and a transcription regulation domain but not a DNA binding domain, but it is not limited thereto.

According to one embodiment of the present invention, the transcription factor may be either MADS box transcription factor or MYB transcription factor, but it is not limited thereto as long as it is a transcription factor which contains a dimerization domain to regulate transcription based on dimerization. The MADS box transcription factor may be SOC1 (SUPPRESSOR OF OVEREXPRESSOR OF CONSTANS 1), BdSOC1 (*Brachypodium distachyon* SUPPRESSOR OF OVEREXPRESSOR OF CONSTANS 1), or AG (AGAMOUS), and the MYB transcription factor may be LHY (LATE ELONGATED HYPOCOTYL), but it is not limited thereto.

According to one embodiment of the present invention, the transcription factors SOC1, BdSOC1, AG and LHY may consist of the amino acid sequence of SEQ ID NO: 1, SEQ ID NO: 2, SEQ ID NO: 3, and SEQ ID NO: 4, respectively, but it is not limited thereto.

For example, the artificial small interfering peptide for the SOC1 transcription factor may be 1-170 amino acids, 30-170, or 82-170 amino acids of the SOC1 transcription factor which consists of the amino acid sequence of SEQ ID NO: 1, but it is not limited thereto. Furthermore, the artificial small interfering peptide for the BdSOC1 transcription factor may be 49-188 amino acids, or 99-188 amino acids of the BdSOC1 transcription factor which consists of the amino acid sequence of SEQ ID NO: 2, but it is not limited thereto. Furthermore, the artificial small interfering peptide for AG transcription factor may be 18-192 amino acids, 77-192 amino acids, 103-192 amino acids, or 103-252 amino acids of the AG transcription factor which consists of the amino acid sequence of SEQ ID NO: 3, but it is not limited thereto. Furthermore, the artificial small interfering peptide for LHY transcription factor may be 100-359 amino acids of the LHY transcription factor which consists of the amino acid sequence of SEQ ID NO: 4, but it is not limited thereto.

The SOC1 transcription factor of the present invention is involved with flowering control in *Arabidopsis thaliana*, and the scope of the SOC1 transcription factor according to the present invention includes a polypeptide having an amino acid sequence represented by SEQ ID NO: 1, which is isolated from *Arabidopsis thaliana*, and also functional equivalents of the polypeptide. The term "functional equivalent" indicates a polypeptide having, as a result of addition, substitution, or deletion of an amino acid, at least 70%, preferably at least 80%, more preferably at least 90%, and even more preferably at least 95% sequence homology with the amino acid sequence represented by SEQ ID NO: 2, and it exhibits substantially the same physiological activity as the protein represented by SEQ ID NO: 1.

The BdSOC1 transcription factor of the present invention is involved with flowering (i.e., heading) of *Brachypodium distachyon*, and the scope of the BdSOC1 transcription factor of the present invention includes the polypeptide which has an amino acid sequence that is represented by SEQ ID NO: 2 as isolated from *Brachypodium distachyon*, and functional equivalent of the polypeptide.

The AG transcription factor of the present invention is involved with forming of flower structure of *Arabidopsis thaliana*, and the scope of the AF transcription factor of the present invention includes the polypeptide which has an amino acid sequence that is represented by SEQ ID NO: 3 as isolated from *Arabidopsis thaliana*, and functional equivalent of the polypeptide.

The LHY transcription factor of the present invention is involved with circadian clock regulation in *Arabidopsis thaliana*, and the scope of the LHY transcription factor of the present invention includes the polypeptide which has an amino acid sequence that is represented by SEQ ID NO: 4 as isolated from *Arabidopsis thaliana*, and functional equivalent of the polypeptide.

According to one embodiment of the present invention, each of transcription factor SOC1, BdSOC1, AG, and LHY may be encoded by the nucleotide sequence of SEQ ID NO: 5, SEQ ID NO: 6, SEQ ID NO: 7, and SEQ ID NO: 8, respectively. The gene of *Arabidopsis thaliana* SOC1 transcription factor of the present invention may consist of the nucleotide sequence represented by SEQ ID NO: 5, but it is not limited thereto. Further, homologues of the nucleotide sequence are also within the scope of the present invention. Homologues indicate a nucleotide sequence with different base sequence but having functional characteristics that are homologous to those of the nucleotide sequence of SEQ ID NO: 5. Specifically, the above described gene may comprise a nucleotide sequence which has preferably at least 70%, more preferably at least 80%, still more preferably at least 90%, and most preferably at least 95% homology with the nucleotide sequence of SEQ ID NO: 5. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

The gene of *Brachypodium distachyon* BdSOC1 transcription factor of the present invention may consist of a nucleotide sequence that is represented by SEQ ID NO: 6, but it is not limited thereto. Homologs of the aforementioned nucleotide sequence are also within the scope of the present invention.

The gene of *Arabidopsis thaliana* AG transcription factor of the present invention may consist of a nucleotide sequence that is represented by SEQ ID NO: 7, but it is not limited thereto. Homologs of the aforementioned nucleotide sequence are also within the scope of the present invention.

The gene of *Arabidopsis thaliana* LHY transcription factor of the present invention may consist of a nucleotide sequence that is represented by SEQ ID NO: 8, but it is not limited thereto. Homologs of the aforementioned nucleotide sequence are also within the scope of the present invention.

The present invention further provides a gene encoding the artificial small interfering peptide, and the homologs of the gene encoding the artificial small interfering peptide are also within the scope of the present invention.

The present invention also provides a recombinant plant vector comprising the gene which encodes the aforementioned artificial small interfering peptide.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding the artificial small interfering peptide can be inserted to a recombinant vector. The term "vector" is used herein to refer DNA fragment(s) and nucleotide molecules that are delivered to a cell. Vector can replicate DNA and be independently reproduced in a host cell. The terms "delivery system" and "vector" are often interchangeably used. The term "recombinant vector" means bacteria plasmid, phage, yeast plasmid, plant cell virus, mammalian cell virus, or other vector. Any plasmid and vector can be generally used if it can replicate and is stabilized in a host. Important characteristics of the expression vector include that it comprises a replication origin, a promoter, a marker gene, and a translation control element.

The expression vector comprising each sequence of the gene encoding the artificial small interfering peptide and an appropriate signal for regulating transcription/translation can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

Preferred example of the recombinant vector of the present invention is Ti-plasmid vector which can transfer a part of itself, i.e., so called T-region, to a plant cell when the vector is present in an appropriate host such as *Agrobacterium tumefaciens*. Other types of Ti-plasmid vector (see, EP 0 116 718 B1) are currently used for transferring a hybrid DNA sequence to protoplasts that can produce a new plant by appropriately inserting a plant cell or hybrid DNA to a genome of a plant. Especially preferred form of Ti-plasmid vector is a so-called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded virus, and a viral vector which can be originated from Gemini virus, etc., for example a non-complete plant viral vector. Use of said vector can be advantageous especially when a host plant cannot be easily transformed.

For the recombinant expression vector according to the present invention, the promoter is a promoter which is suitable for transformation and it is preferably any of CaMV 35S promoter, actin promoter, ubiquitin promoter, pEMU promoter, MAS promoter, histone promoter, or C1p promoter, but not limited thereto. The term "promoter" means a DNA molecule to which RNA polymerase binds in order to initiate its transcription, and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, the constitutive promoter can be preferable for the present invention. Therefore, a possibility for choosing the constitutive promoter is not limited herein.

For the recombinant vector of the present invention, any conventional terminator can be used. Examples include nopaline synthase (NOS), rice α-amylase RAmy 1 A terminator, phaseoline terminator, a terminator for optopine gene of *Agrobacterium tumefaciens*, a phaseoline terminator, and rnnB1/B2 terminator of *E. Coli*, but are not limited thereto. Regarding the necessity of terminator, it is generally known that such region can increase reliability and an efficiency of transcription in plant cells. Therefore, the use of terminator is highly preferable in view of the contexts of the present invention.

The recombinant vector may comprise at least one selective marker. Said selective marker is a nucleotide sequence having a property of being selected by a common chemical method. Examples include all genes that are useful for distinguishing transformed cells from non-transformed cells. Specific examples thereof include a gene resistant to herbicide such as glyphosate and phosphinotricine, a gene resistant to antibiotics such as kanamycin, G418, bleomycin, hygromycin, and chloramphenicol, and aadA gene, but not limited thereto.

The present invention further provides a plant transformed with the recombinant plant vector to have inhibited transcription factor activity.

The step of transforming a plant cell with the recombinant vector of the present invention means any method by which DNA is delivered to a plant. Such transformation method does not necessarily need a period for regeneration and/or tissue culture. Transformation of plant species is now quite general not only for dicot plants but also for monocot plants. In principle, any transformation method can be used for introducing a hybrid DNA of the present invention to appropriate progenitor cells. The method can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio. Technol. 3, 1099-1102), a microscopic injection method for plant components (Crossway A. et al., 1986, Mol. Gen. Genet. 202, 179-185), a particle bombardment method for various plant components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. A method preferred in the present invention includes *Agrobacterium* mediated DNA transfer. In particular, so-called binary vector technique as disclosed in EPA 120 516 and U.S. Pat. No. 4,940,838 can be preferably adopted for the present invention.

The present invention further provides a method for inhibiting transcription factor activity of a plant comprising transforming a plant cell with the recombinant vector comprising the gene encoding the artificial small interfering peptide to overexpress the gene encoding the artificial small interfering peptide.

The present invention further provides a method for producing a transgenic plant with inhibited transcription factor activity comprising transforming a plant cell with the recombinant vector comprising the gene encoding the artificial small interfering peptide to overexpress the gene encoding the artificial small interfering peptide.

The method for transforming a plant cell is as described above.

The present invention further provides a transgenic plant having inhibited transcription factor activity which is produced by the aforementioned method, and a seed thereof.

According to one embodiment of the present invention, the plant can be either a monocot plant or a dicot plant. Preferred examples of the plant include food crops that are selected from a group consisting of rice, wheat, barley, corn, soybean, potato, wheat, red bean, oat, and sorghum; vegetable crops selected from a group consisting of *Arabidopsis thaliana*, Chinese cabbage, daikon, pepper, strawberry, tomato, watermelon, cucumber, cabbage, oriental melon, zucchini, scallion, onion, and carrot; special crops selected from a group consisting of *ginseng*, tobacco, cotton, sesame, sugar cane, sugar beet, wild sesame, peanut, and canola; fruits selected from a group consisting of apple, pear, date, peach, kiwi, grape, tangerine, persimmon, plum, apricot and banana; flowers selected from a group consisting of rose, *gladiolus, gerbera*, carnation, *chrysanthemum*, lily and tulip, and feed crops selected from a group consisting of *Brachypodium distachyon*, rye grass, red clover, orchard grass, alfalfa, tall fescue, and perennial grass. More preferably, it is *Arabidopsis thaliana* or *Brachypodium distachyon*, but not limited thereto.

The present invention further provides a composition for inhibiting transcription factor activity of a plant which comprises a recombinant vector comprising a gene encoding the artificial small interfering peptide. With this composition, a plant can be transformed with a recombinant vector comprising, as an effective component, the gene encoding the artificial small interfering peptide, and thus the transcription activity of a plant is inhibited and the transcription regulated by the transcription factor can be inhibited.

Herein below, the present invention is explained in greater detail in view of the Examples. However, it is evident that the following Examples are given only for exemplification of the present invention and by no means the present invention is limited to the following Examples.

Materials and Methods

1. Plant Materials and Growth Conditions

All *Arabidopsis thaliana* (*Arabidopsis*) lines used were in the Columbia (Col-0) background. *Arabidopsis* plants were grown in a controlled culture room at 23° C. with relative humidity of 55% under long day conditions (LD, 16-h light/8-h dark) with white light illumination (120 µmol photons/m²s) provided by fluorescent FLR40D/A tubes (Osram, Seoul, Korea). The *Arabidopsis* loss-of-function soc1-2 and activation-tagged soc1-101D mutants have been described previously (Moon et al., Plant J. 35:613-623, 2003). The T-DNA insertional ag-3 knockout mutant (SALK-014999) was obtained from the *Arabidopsis* Biological Resource Center (ABRC). The cca1-2 mutant has been described previously (Seo et al., Plant Cell. 24(6): 2427-2442, 2012).

*Brachypodium distachyon* (*Brachypodium*) Bd21-3, a community standard diploid inbred line, was used in this study. *Brachypodium* plants were grown in a controlled growth chamber with relative humidity of 60% under LD. The LD condition was 20-h light/4-h dark with white light illumination (150 µmol photons/m²s) provided by fluorescent FLR40D/A fluorescent tubes (Osram). Growth temperatures were 24° C. during the day and 18° C. at night.

2. Generation of Artificial Small Interfering PEP (a-siPEP) Constructs

Inventors of the present invention referred to the protein domain structures of the *Arabidopsis* AGAMOUS (AG, At4g18960) and SUPPRESSOR OF OVEREXPRESSION OF CONSTANS 1 (SOC1, At2g45660) transcription factors that have been predicted previously (Kaufmann et al., Gene, 347, 183-198, 2005). Gene sequences encoding specific protein domains, such as MADS, K (keratin-like), I (intervening), C (C-terminal), and combinations of the domains, were obtained by RT-PCR using gene-specific primer pairs. Inventors of the present invention also referred to the earlier studies (Lu et al., Plant Physiol. 150, 834-843, 2009) describing the protein domain structure of *Arabidopsis* LHY transcription factor (At1g01060) and designated primer pairs to amplify the dimerization domain. The PCR products were fully sequenced in both directions to confirm the sequence contexts. Artificial start codon and stop codons were incorporated into the 5' end and 3' end primers, respectively. The RT-PCR primers used are listed in Table 1.

TABLE 1

| Primer name | Use | Primer sequence | SEQ ID NO: |
|---|---|---|---|
| eIF4a-F | qRT-PCR | 5'-TGACCACACAGTCTCTGCAA | 9 |
| eIF4a-R | qRT-PCR | 5'-ACCAGGGAGACTTGTTGGAC | 10 |
| SOC1-F | qRT-PCR | 5'-GGATCTCATGAAAGCGAAGTTT | 11 |
| SOC1-R | qRT-PCR | 5'-TCACTTTCTTGAAGAACAAGGTA | 12 |
| SOC1-K-F | qRT-PCR | 5'-AAGAAAATATGCAGCATTTGAAATA | 13 |
| SOC1-K-R | qRT-PCR | 5'-CCTATGCCTTCTCCCAAGAGT | 14 |
| AP1-F | qRT-PCR | 5'-TGATGCTGAAGTTGCTCTTGTT | 15 |
| AP1-R | qRT-PCR | 5'-CGACCAGTTTGTATTGACGTCG | 16 |
| CAL-F | qRT-PCR | 5'-GGGAAGGGGTAGGGTTGAAT | 17 |
| CAL-R | qRT-PCR | 5'-ACAATAAGGGAAACCTCGGC | 18 |
| FUL-F | qRT-PCR | 5'-ATGATGGAACTCCGTTGTCG | 19 |
| FUL-R | qRT-PCR | 5'-TTCATGAGAAATCATTACCAAGATATG | 20 |
| LFY-F | qRT-PCR | 5'-TTACTGGGACGCAGGTCAAG | 21 |
| LFY-R | qRT-PCR | 5'-CCCAAACCACTACCTCCGTT | 22 |
| SPL3-F | qRT-PCR | 5'-ACAATGCAGCAGGTTTCACG | 23 |
| SPL3-R | qRT-PCR | 5'-CTTTTCCGCCTTCTCTCGTT | 24 |
| SPL5-F | qRT-PCR | 5'-GATCAGATAAACCCTCCCGC | 25 |
| SPL5-R | qRT-PCR | 5'-ACCATGACCAACTTTTCTTGACA | 26 |
| SPL8-F | qRT-PCR | 5'-CGCCGTAAATGTCACCAATC | 27 |
| SPL8-R | qRT-PCR | 5'-GAAGACGCTGTCGTTTGGAA | 28 |
| AG-F | qRT-PCR | 5'-TCAACCGTTTGATTCACGG | 29 |
| AG-R | qRT-PCR | 5'-TTACACTAACTGGAGAGCGGTTT | 30 |

TABLE 1-continued

| Primer name | Use | Primer sequence | SEQ ID NO: |
|---|---|---|---|
| AG-K-F | qRT-PCR | 5'-CTCAGGAACTTGGAAGGCAG | 31 |
| AG-K-R | qRT-PCR | 5'-ATCAACTTCTCTTTTCTGCATGTAGT | 32 |
| DAD1-F | qRT-PCR | 5'-TTCGTGCCACGTCAGGTATT | 33 |
| DAD1-R | qRT-PCR | 5'-TCTTTGTCCTGGCAAACTGC | 34 |
| GIK-F | qRT-PCR | 5'-GTAATGGTCATGGCAGCGTC | 35 |
| GIK-R | qRT-PCR | 5'-ACATATTCCCTCCACCTCCG | 36 |
| TOC1-F | qRT-PCR | 5'-TCTTCGCAGAATCCCTGTGAT | 37 |
| TOC1-R | qRT-PCR | 5'-GCTGCACCTAGCTTCAAGCA | 38 |
| S-M-F | Subcloning | 5'-AAAAAGCAGGCTCTATGGTGAGGGGCAAAACT | 39 |
| S-M-R | Subcloning | 5'-AGAAAGCTGGGTTTCAGGAGCTGGCGAATTCATA | 40 |
| S-MIK-F | Subcloning | 5'-AAAAAGCAGGCTCTATGGTGAGGGGCAAAACT | 41 |
| S-IK-F | Subcloning | 5'-AAAAAGCAGGCTCTATGAAGAAAGCCTTTGAGCTCTCA | 42 |
| S-K-F | Subcloning | 5'-AAAAAGCAGGCTCTATGGTTTCTGAAGAAAATATGCAGC | 43 |
| S-K-R | Subcloning | 5'-AGAAAGCTGGGTTTCACCACTTTTCAGAGAGCTTCTC | 44 |
| AG-F | Subcloning | 5'-AAAAAGCAGGCTCTATGGCGGCGTACCAATCGG | 45 |
| AG-R | Subcloning | 5'-AGAAAGCTGGGTTTTACACTAACTGGAGAGCGGT | 46 |
| AG-M-F | Subcloning | 5'-AAAAAGCAGGCTCTATGGGGAGAGGAAAGATCGAAATCAAACGG | 47 |
| AG-M-R | Subcloning | 5'-AGAAAGCTGGGTTTTAGTTGTTAGAGTACTCATAGAGACGACCACG | 48 |
| AG-I-F | Subcloning | 5'-AAAAAGCAGGCTCTATGAGTGTAAAAGGGACTATTGAGAGGT | 49 |
| AG-I-R | Subcloning | 5'-AGAAAGCTGGGTTTTAGTCCGATATTGCCTTCTTGTACCTCTC | 50 |
| AG-K-F | Subcloning | 5'-AAAAAGCAGGCTCTATGAATTCTAACACCGGATCGGTGGCAGAA | 51 |
| AG-K-R | Subcloning | 5'-AGAAAGCTGGGTTTTAATCAACTTCTCTTTTCTGCATGTAGTCGATTTC | 52 |
| AG-C-F | Subcloning | 5'-AAAAAGCAGGCTCTATGTTGCATAACGATAACCAGATTCTTC | 53 |
| LHY-DD-F | Subcloning | 5'-AAAAAGCAGGCTCTATGAATACTCCTTATCCTCGAAAGCCTG | 54 |
| LHY-DD-R | Subcloning | 5'-AGAAAGCTGGGTTTAAGCCCACCAAGCAGTTGC | 55 |
| SOC1-F | Y2H | 5'-GGAATTCCATATGATGGTGAGGGGCAAAAC | 56 |
| SOC1-R | Y2H | 5'-CGGGATCCTCACTTTCTTGAAGAACAAGGTA | 57 |
| S-MIK-F | Y2H | 5'-GGAATTCCATATGATGGTGAGGGGCAAAAC | 58 |
| S-IK-F | Y2H | 5'-GGAATTCCATATGAAGAAAGCCTTTGAGCTCTC | 59 |
| S-K-F | Y2H | 5'-GGGAATTCGTTTCTGAAGAAAATATGCAGC | 60 |
| S-K-R | Y2H | 5'-CGGGATCCCCACTTTTCAGAGAGCTTCTC | 61 |
| S-MIK-F | Y3H | 5'-TCAGCGGCCGCGATGGTGAGGGGCAAAAC | 62 |
| S-IK-F | Y3H | 5'-TCAGCGGCCGCGATGAAGAAAGCCTTTGAGCTC | 63 |
| S-K-F | Y3H | 5'-TCAGCGGCCGCGATGGTTTCTGAAGAAAATATGCA | 64 |
| S-K-R | Y3H | 5'-GAAGATCTTCACCACTTTTCAGAGAGCTTC | 65 |
| SOC1-nEYFP-F | BiFC | 5'-CCGCTCGAGGGATGGTGAGGGGCAAAACTCA | 66 |
| SOC1-nEYFP-R | BiFC | 5'-CGGGATCCTCACTTTCTTGAAGAACAAGGTAACC | 67 |
| SOC1-cEYFP-R | BiFC | 5'-GCGGATCCCCCTTTCTTGAAGAACAAGGTAACCC | 68 |
| S-MIK-cEYFP-F | BiFC | 5'-CCGCTCGAGCATGGTGAGGGGCAAAACTCA | 69 |

TABLE 1-continued

| Primer name | Use | Primer sequence | SEQ ID NO: |
|---|---|---|---|
| S-IK-cEYFP-F | BiFC | 5'-CCGCTCGAGCATGAAGAAAGCCTTTGAGCTCTCA | 70 |
| S-K-cEYFP-F | BiFC | 5'-CCGCTCGAGCATGGTTTCTGAAGAAAATATGCAG | 71 |
| S-K-cEYFP-R | BiFC | 5'-GCGGATCCCCCACTTTTCAGAGAGCTTCTCGTTT | 72 |
| SOC1-F | TAA | 5'-TCCCCCGGGATGGTGAGGGGCAAAACTC | 73 |
| SOC1-R | TAA | 5'-TCCCCCGGGTCACTTTCTTGAAGAACAAGGTAAC | 74 |

A putative *Brachypodium* BdSOC1 (Bradi1g77020) gene was identified by BLAST search (http://blast.ncbi.nlm.nih.gov/Blast.cgi) of the *Brachypodium* genome database (http://www.*brachypodium*.org/) against the *Arabidopsis* SOC1 gene as bait. Structural domain organization of the BdSOC1 protein was also analyzed in comparison to that of the *Arabidopsis* SOC1 protein. Truncated BdSOC1 gene constructs were generated according to the sequence contexts that were defined with the *Arabidopsis* SOC1 gene. The RT-PCR primers used are listed in Table 2.

TABLE 2

| Primer name | Use | Primer sequence | SEQ ID NO: |
|---|---|---|---|
| BdUBC18-F | qRT-PCR | 5'-GGAGGCACCTCAGGTCATTT | 75 |
| BdUBC18-R | qRT-PCR | 5'-ATAGCGGTCATTGTCTTGCG | 76 |
| BdSOC1-F | qRT-PCR | 5'-TACGCTGGTGACCTCTGCTC | 77 |
| BdSOC1-R | qRT-PCR | 5'-GGTTCTCCTCCTCCTCCTCC | 78 |
| BdS-K-F | qRT-PCR | 5'-AAGAGCCTTCGTAGCATCAGG | 79 |
| BdS-K-R | qRT-PCR | 5'-CGCAACGTCATCTCCTTCTG | 80 |
| BdAP1-F | qRT-PCR | 5'-CAAGATAAACCGGCAGGTGA | 81 |
| BdAP1-R | qRT-PCR | 5'-CCCTTGGTGGAGAAGACGAT | 82 |
| BdCAL-F | qRT-PCR | 5'-TTCGCCACCGACTCATGTAT | 83 |
| BdCAL-R | qRT-PCR | 5'-CGTGACACCAGTTTCCCTGA | 84 |
| BdFUL-F | qRT-PCR | 5'-GCAGGAGGAGAACAAGGCTC | 85 |
| BdFUL-R | qRT-PCR | 5'-CTGTTCCCACTGCACTTGCT | 86 |
| BdLFY-F | qRT-PCR | 5'-GAAGTGTTGTCGAACGAGCG | 87 |
| BdLFY-R | qRT-PCR | 5'-CCATTCCTCTGCTTCTTCCC | 88 |
| BdSPL8-F | qRT-PCR | 5'-TACGACAGCTTCGACTTCGC | 89 |
| BdSPL8-R | qRT-PCR | 5'-GGGTGGTGGAGTAGGTTGCT | 90 |
| BdSOC1-F | Subcloning | 5'-GCTCTAGAATGCAGGCAGGCCGGCTCGATCGG | 91 |
| BdSOC1-R | Subcloning | 5'-GCGGATCCGAGAGCGATTTCTGCCGGGCAGTC | 92 |
| BdS-MK1-F | Subcloning | 5'-GCTCTAGAATGGTGCGGGGGAAGACGCAGCTG | 93 |
| BdS-MK2-F | Subcloning | 5'-GCTCTAGAATGAAGGCGCACGAGCTCTCCGTCCTCTG | 94 |
| BdSOC1-K-F | Subcloning | 5'-GCTCTAGAATGACGGCACAGCAAGACATAG | 95 |
| BdSOC1-K-R | Subcloning | 5'-GCGGATCCGCACCTTGCCCCTTAGATCTTCGTTCTC | 96 |
| BdSOC1-F | in vitro translation | 5'-CGCGCGATCGCATGCAGGCAGGCCGGCTCGATCGG | 97 |
| BdSOC1-R | in vitro translation | 5'-TCGTTTAAACTCAAGAGCGATTTCTGCCGGGCAGTC | 98 |
| BdS-MK1-F | in vitro translation | 5'-CGCGCGATCGCATGGTGCGGGGGAAGACGCAGCTGAAG | 99 |
| BdS-MK2-F | in vitro translation | 5'-CGCGCGATCGCATGAAGGCGCACGAGCTCTCCGTCC | 100 |

TABLE 2-continued

| Primer name | Use | Primer sequence | SEQ ID NO: |
|---|---|---|---|
| BdS-K-F | in vitro translation | 5'-CGCGCGATCGCATGACGGCACAGCAAGACATAG | 101 |
| BdS-K-R | in vitro translation | 5'-TCGTTTAAACTCACACCTTGCCCCTTAGATCTTCGTTC | 102 |
| BdSOC1-F | MBP/GFP fusion | 5'-AAAAAGCAGGCTCTATGCAGGCAGGCCGGCTCGATCGGAGAGG | 103 |
| BdSOC1-R | MBP/GFP fusion | 5'-AGAAAGCTGGGTTTCAAGAGCGATTTCTGCCGGGCAGTCCGATGAACAGCTC | 104 |
| BdS-M-F | GFP fusion | 5'-AAAAAGCAGGCTCTATGGTGCGGGGAAGACGCAGCTGAAGCGG | 105 |
| BdS-M-R | GFP fusion | 5'-AGAAAGCTGGGTTTCAGCTGGCGAACTCGTAGAGGCGGCCGCTGGGGG | 106 |
| BdS-MK1-F | GFP fusion | 5'-AAAAAGCAGGCTCTATGGTGCGGGGAAGACGCAGCTGAAGCGG | 107 |
| BdS-MK2-F | GFP fusion | 5'-AAAAAGCAGGCTCTATGAAGGCGCACGAGCTCTCCGTCCTCTGCG | 108 |
| BdS-K-F | GFP fusion | 5'-AAAAAGCAGGCTCTATGACGGCACAGCAAGACATAGAGAAGATAA | 109 |
| BdS-K-R | GFP fusion | 5'-AGAAAGCTGGGTTTTACACCTTGCCCCTTAGATCTTCGTTCTCCTTG | 110 |
| BdS-K-F | GST fusion | 5'-CGGGATCCATGACGGCACAGCAAGACATAG | 111 |
| BdS-K-R | GST fusion | 5'-GGAATTCCTTACACCTTGCCCCTTAGATCTTCG | 112 |
| BdSOC1-F | BiFC | 5'-TCGAATTCTATGCAGGCAGGCCGGCTCGATCGG | 113 |
| BdSOC1-R | BiFC | 5'-GGTGGATCCTCAAGAGCGATTTCTGCCGGGCAGTC | 114 |
| BdS-MK1-F | BiFC | 5'-GCTCAAGCTTCGATGGTGCGGGGAAGACGCAGCTGAAG | 115 |
| BdS-MK2-F | BiFC | 5'-GCTCAAGCTTCGATGAAGGCGCACGAGCTCTCCGTCCTCTG | 116 |
| BdS-K-F | BiFC | 5'-GCTCAAGCTTCGATGACGGCACAGCAAGACATAGAGAAGATA | 117 |
| BdS-K-R | BiFC | 5'-CGCGGTACCTTACACCTTGCCCCTTAGATCTTCGTTCTCCTTG | 118 |

3. Plant Transformation

To produce transgenic *Arabidopsis* plants overexpressing SOC1, AG, and LHY genes, the gene sequences were subcloned into the binary pB2GW7 vector under the control of the Cauliflower Mosaic Virus (CaMV) 35S promoter (Invitrogen, Carlsbad, Calif.). *Agrobacterium*-mediated *Arabidopsis* transformation was carried out according to a modified floral dip method (Clough and Bent, Plant J. 16, 735-743, 1998). $T_1$ seeds were sown in soil, and sprayed twice a week with a 1:1,000 dilution (in water) of Finale solution (AgrEvo, Montvale, N.J.) containing 5.78% Basta. Homozygotic transgenic plants having single T-DNA insertional event were obtained by herbicide selection for two additional generations and analysis of segregation ratios.

The BdSOC1 gene sequences amplified from *Brachypodium* cDNA pool were subcloned into the binary pJJ461 vector under the control of the CaMV 35S promoter. The pJJ461 vector was kindly provided by Dr. Jong-Seong Jeon (Kyung Hee University, Seoul, Korea). *Brachypodium* transformation was performed according to the *Agrobacterium*-mediated method using compact embryogenic calli derived from immature embryos of the diploid inbred line Bd21-3 (Vogel and Hill, Plant Cell Rep. 27, 471-478, 2008). T3 transgenic *Brachypodium* plants were used in all assays.

4. Analysis of mRNA Levels

Quantitative real-time RT-PCR (qRT-PCR) was employed to measure mRNA levels. Total RNA preparation, reverse transcription, and quantitative polymerase chain reaction were carried out based on the rules that have been proposed to ensure reproducible and accurate measurements of mRNA levels (Udvardi et al., Plant Cell, 20, 1736-1737, 2008). Extraction of total RNA samples from appropriate plant materials and RT-PCR conditions have been described previously. Total RNA samples were pretreated extensively with an RNAse-free DNAse to get rid of contaminating genomic DNA before use.

qRT-PCR reactions were carried out in 96-well blocks using an Applied Biosystems 7500 Real-Time PCR System using the SYBR Green I master mix in a reaction volume of 25 □L. The PCR primers were designed using the Primer Express Software installed into the system. The two-step thermal cycling profile used was 15 sec at 94° C. and 1 min at 68° C. An EUKARYOTIC TRANSLATION INITIATION FACTOR 4A1 (eIF4A) gene (At3g13920) was included in the reactions as internal control for normalizing the variations in cDNA amounts used. All qRT-PCR reactions were carried out in biological triplicates using total RNA samples extracted from three independent replicate samples of plants grown under identical conditions. The comparative □□$C_T$ method was employed to evaluate relative quantities of each amplified product in the samples. The threshold cycle ($C_T$) was automatically determined for each reaction by the system set with default parameters. The specificity of the qRT-PCR reactions was determined by melt curve analysis of the amplified products using the standard method installed in the system.

5. Flowering Time Measurements

*Arabidopsis* plants were grown in soil at 23° C. under LD (16-h light/8-h dark). Flowering times were measured by counting the number of rosette leaves at bolting. Fifteen to twenty plants were counted and averaged for each measurement.

*Brachypodium* plants were planted in Sunshine Professional Growing Mix 1 (SUN GRO Horticulture, Bellevue, Wash.) and then subsequently placed in a controlled growth chamber under LD (20-h light/4-h dark). Flowering times were scored by counting the days at heading emergence. Twenty plants were counted and averaged for each measurement.

6. Subcellular Localization Assays

For detection by fluorescence microscopy, the green fluorescent protein (GFP)-coding sequence was fused in-frame to the 3' ends of the *Arabidopsis* SOC1 gene sequences, and the gene fusions were subcloned into the pB7FWG2 vector (Invitrogen). The expression constructs were transformed into *Arabidopsis* protoplasts by polyethylene glycol (PEG)-mediated calcium transfection (Yoo et al., Nat. Protoc. 2, 1565-1572, 2007). The subcellular distribution of the SOC1 proteins was visualized by differential interference contrast microscopy (DIC) and fluorescence microscopy. The GFP fusion proteins were excited at 488 and 568 nm, and the green fluorescence signals were filtered with the HQ600/50 emission filter (Chroma, Rockingham, Vt.). The autofluorescence of chlorophylls was excited at 568 nm and emitted with the E600LP filter (Nikon, Tokyo, Japan). The merged signals were obtained using the Zeiss LSM image browser (Carl Zeiss, Jena, Germany).

*Brachypodium* BdSOC1 gene was similarly fused to the GFP-coding sequence, and the fusion constructs were subcloned into the pB7FWG2 vector (Invitrogen). *Brachypodium* protoplasts were isolated from the third leaves of 2-week-old *Brachypodium* seedlings, according to the procedure for *Arabidopsis* protoplast preparation. The BdSOC1 fusion constructs were expressed transiently in the *Brachypodium* protoplasts, and the green fluorescence signals were detected and analyzed as described above with the assays in *Arabidopsis* protoplasts.

7. Transcriptional Activity Assays

For transient expression assays in *Arabidopsis* protoplasts, several reporter and effector plasmids were constructed. The reporter plasmid contains four copies of the GAL4 upstream activation sequence (UAS) and the □-glucuronidase gene (GUS). To construct the p35S:SOC1 effector plasmid, the SOC1 gene sequences were fused to the GAL4 DNA binding domain and inserted into an expression vector containing the CaMV 35S promoter. The reporter and effector plasmids were cotransformed into *Arabidopsis* protoplasts by a PEG-mediated transformation method (Yoo et al., Nat. Protoc. 2, 1565-1572, 2007). GUS activities were measured by the fluorometric method as described previously (Yang et al., Plant Cell, 23, 2155-2168, 2011). A CaMV 35S promoter-luciferase (LUC) construct was also cotransformed as internal control, and the luciferase assay was carried using the Luciferase Assay System kit (Promega, Madison, Wis.).

8. In Vitro Pull-Down Assays

Recombinant maltose-binding protein (MBP) and MBP-SOC1 and MBP-BdSOC1 proteins were produced in *Escherichia coli* BL21-CodonPlus (DE3)-RIL strain (Stratagene, Santa Clara, Calif.) and partially purified as follows. One-tenth volume of precultured cells (5 mL) was transferred to 500 mL of fresh Luria-Bertani (LB) medium and cultured at 37° C. until $OD_{600}$ reached 0.3 to 0.6. Protein production was induced by adding isopropyl-β-D-thiogalactopyranoside (IPTG) at a final concentration of 0.5 mM and shaking at 37° C. for 5 h. Cells were harvested and resuspended in buffer A [25 mM HEPES, pH 7.5, 20% glycerol, 1 mM DTT, 100 mM NaCl, 0.2 mM EDTA with protease inhibitor cocktail (Sigma-Aldrich, St. Louis, Mo.), and 1 mM PMSF]. The cells were lysed using a French press (8500 p.s.i.; one time). The cell lysates were sonicated for 30 sec twice and centrifuged at 20,000×g for 20 min. The supernatants were stored at −80° C. until use. The truncated SOC1 proteins were also prepared by in vitro translation. The SOC1 and BdSOC1 cDNAs were subcloned into the pGADT7 vector. The SOC1 polypeptides were labeled with $^{35}$S-Met using the TNT®-coupled reticulocyte lysate system (Promega).

The MBP or MBP fusion proteins were mixed with amylose resin (Sigma-Aldrich) and agitated for 15 min at room temperature (23-25 r). The beads were then washed three times with 1×PBS (phosphate-buffered saline) buffer and one time with fresh buffer A. Five □L of the $^{35}$S-labeled polypeptides was added and incubated for 2 h at 4° C. The beads were then washed five times with fresh buffer A. The bound proteins were eluted with 1×SDS loading buffer by boiling for 5 min and subject to SDS-PAGE and autoradiography.

9. Yeast Two-Hybrid Assays

Yeast two-hybrid assays were performed using the BD Matchmaker system (Clontech, Mountain View, Calif.). The pGADT7 vector was used for GAL4 AD (activation domain) fusion, and the pGBKT7 vector was used for GAL4 BD (DNA-binding domain) fusion. The yeast strain AH109 (leu-, trp-, ade-, his-), which has chromosomally integrated reporter genes lacZ and HIS under the control of the GAL1 promoter, was used for transformation. The PCR product of SOC1 gene was digested with EcoRI and BamHI and subcloned into the pGBKT7 and pGADT7 vectors. Transformation of the AH109 cells was carried out according to the manufacturer's instruction. Colonies obtained were streaked on a medium without His, Ade, Leu, and Trp. To confirm the results of cell growth assays, β-galactosidase (β-Gal) assays were also carried out according to the system procedure.

The pBridge vector (Clontech) was used for yeast three-hybrid screening. The SOC1 cDNA was amplified by RT-PCR, and the PCR products were digested with EcoRI and BamHI and subcloned into the pBridge vector, resulting in the BD-SOC1 construct. The SOC1 cDNA was also subcloned into the pBridge vector double-digested with NotI and BglII so that their expression was controlled by the methionine-repressible pMET25 promoter. The expression constructs were cotransformed into yeast AH109 cells. The colonies were streaked on media without Leu, Trp, and His supplemented with or without methionine.

10. Bimolecular Fluorescence Complementation (BiFC) Assays

BiFC assays were carried out as described previously (Hong et al., J. Biol. Chem. 286, 1659-1668, 2011). A full-size SOC1 gene was fused in-frame to the 5' end of a gene sequence encoding the C-terminal half of EYFP in the pSATN-cEYFP-C1 vector (E3082). Truncated SOC1 gene sequences were fused in-frame to the 5' end of a gene sequence encoding the N-terminal half of EYFP in the pSATN-nEYFP-C1 vector (E3081). The expression constructs were cotransformed into *Arabidopsis* protoplasts. Expression of the fusion constructs was monitored by fluorescence microscopy using a Zeiss LSM510 confocal microscope (Carl Zeiss MicroImaging GmbH, Jena, Germany). The BdSOC1 gene constructs were prepared similar to the *Arabidopsis* SOC1 gene constructs and transiently expressed in *Brachypodium* protoplasts.

11. Electrophoretic Mobility Shift Assays (EMSA)

The SOC1 gene was subcloned into the pMAL-c2× *E. coli* expression vector (NEB, Ipswich, Mass.) having a MBP-coding sequence. The MBP fusion protein prepared in *E. coli* cells was purified according to the manufacturer's procedure using the pMAL® Protein Fusion and Purification System (#E8000S). The DNA fragments were end-labeled with □-32P [dATP] using T4 polynucleotide kinase. Labeled probes were incubated with approximately one □g of the purified MBP fusion proteins for 30 min at 25° C. in binding buffer (10 mM Tris-HCl, pH 7.6, 50 mM NaCl, 1 mM EDTA, 5 mM DTT, 5% glycerol) with or without competitor DNA fragments. The reaction mixtures were analyzed on 6% native PAGE gels. The gels were dried on Whatman 3MM paper and exposed to X-ray films.

EXAMPLE 1 a-siPEP Overproduction Leads to SOC1-Deficient Phenotypes in *Arabidopsis*

It has been estimated that at least 80 potential siPEPs are encoded by the *Arabidopsis* genome (Seo et al., Trends Plant Sci. 16, 541-549, 2011). Structural analysis of the genomic siPEPs identified so far depicts that they generally possess dimerization domains but lack other protein domains that are required for DNA binding and transcriptional regulation.

Figure 1:
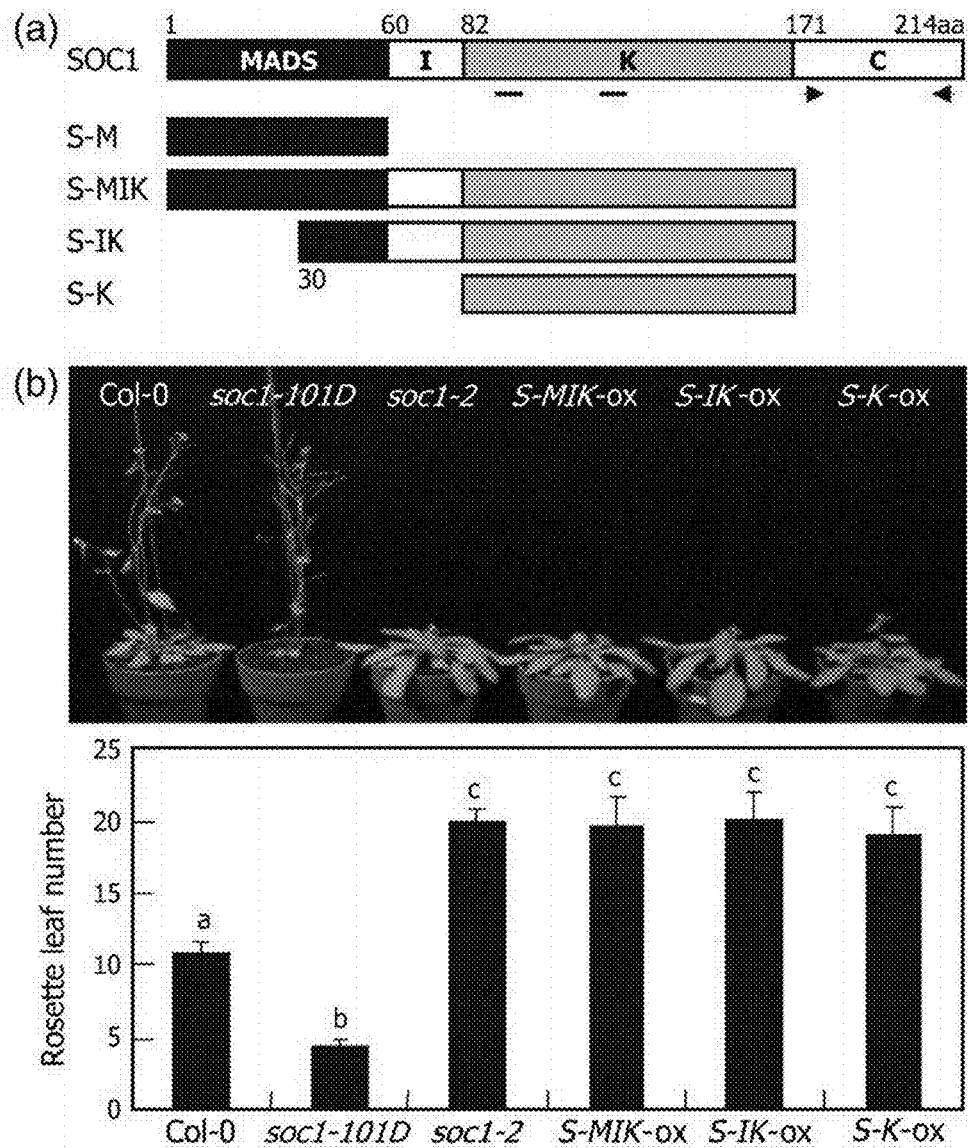
FIG. 1 shows targeted inactivation of SOC1 by a-siPEPs.
(a) Domain structures of SOC1 proteins. Numbers indicate residue positions. Arrowheads and bold bars indicate the positions of SOC1 and S-K primers used to detect SOC1 and S-K transcripts, respectively. aa, amino acids.
(b) Flowering phenotypes. Five-week-old plants grown in soil were photographed (top panel). The SOC1-overexpressing soc1-101D and SOC1-deficient soc1-2 mutants were included for comparison. Rosette leaf numbers of ~20 plants were averaged and statistically treated (bottom panel). Different letters represent significant difference at P<0.05 (one-way ANOVA with Fisher's post hoc test). Bars indicate standard error of the mean.

The *Arabidopsis* SOC1 transcription factor has four distinct domains. The MADS domain is responsible for DNA binding, and the K (keratin-like) domain mediates protein-protein interactions (FIG. 1a). The I (intervening) domain also contributes to SOC1-SOC1 homodimer formation. The C-terminal region performs diverse functions in transcriptional regulation (Kaufmann et al., Gene, 347, 183-198, 2005). Based on the structural criteria defined by the known siPEPs, inventors of the present invention designed a series of potential a-siPEPs of the SOC1 transcription factor (FIG. 1a).

The SOC1 a-siPEP-coding gene sequences were transformed into *Arabidopsis*, and phenotypes of the transgenic plants were compared to those of loss-of-function and activation-tagged mutants (soc1-2 and soc1-101D, respectively). Strikingly, the transgenic plants overproducing the truncated SOC1 forms, such as S-MIK-ox, S-IK-ox, and S-K-ox, exhibited delayed flowering like the soc1-2 mutant (FIG. 1b), suggesting that ectopic expression of the truncated SOC1 forms containing the K domain efficiently suppresses the SOC1 activity. The S-M-ox transgenic plants that overexpress the MADS domain also showed slightly delayed flowering, which is certainly because the MADS domain competes with SOC1 for DNA binding, although they do not form heterodimers.

Figure 2:
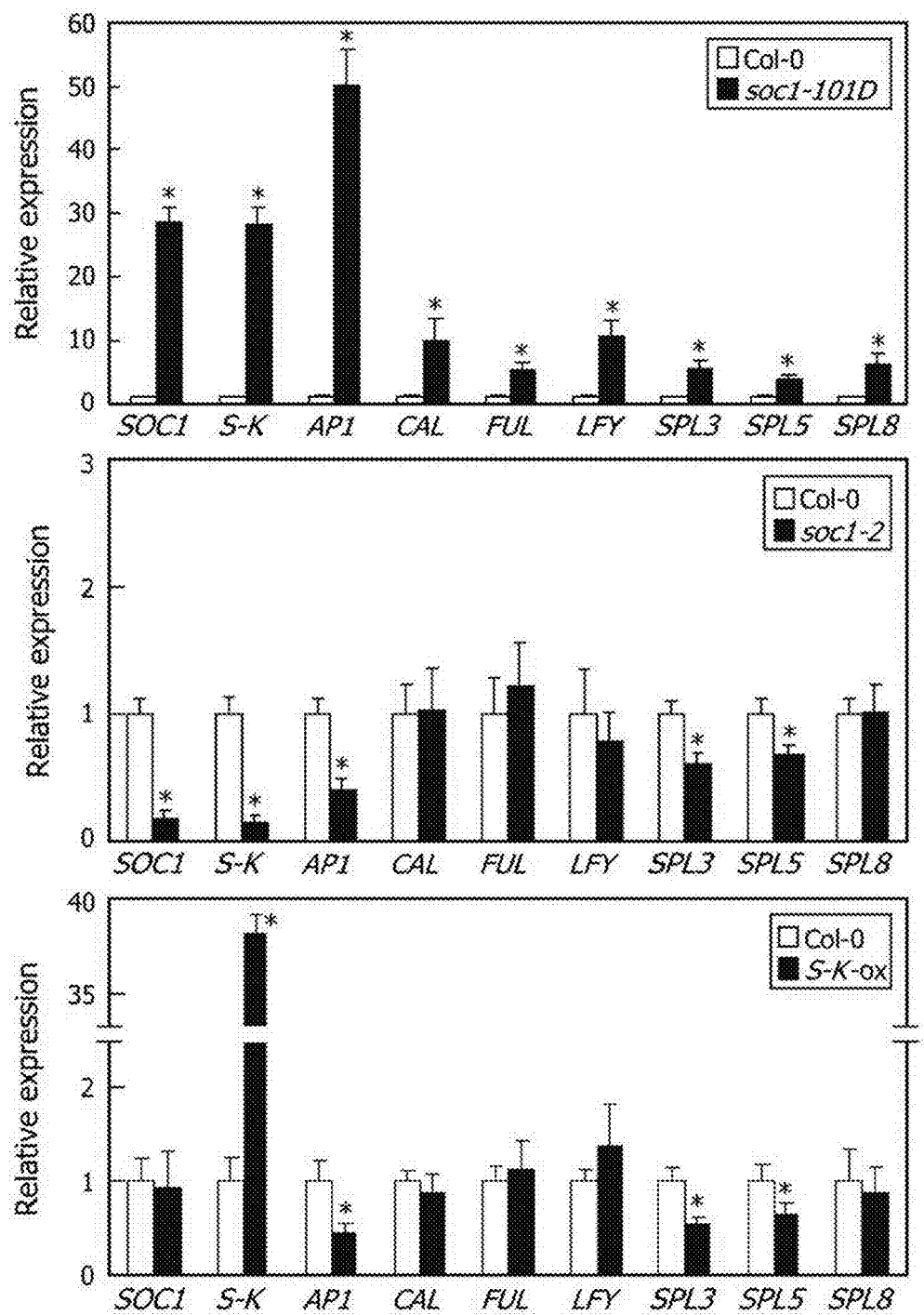
FIG. 2 shows transcript accumulation of SOC1 and its downstream genes.
Two-week-old plants grown on ½× Murashige and Skoog-agar plates (hereafter referred to as MS-agar plates) under long days (LDs) were used for total RNA extraction. mRNA levels of genes acting downstream of SOC1, such as AP1, CAL, FUL, LFY, and SPLs, and encoding the S-K domain were examined by qRT-PCR. Biological triplicates were averaged and statistically treated using a Student's t-test (*P<0.01). Bars indicate standard error of the mean.

Inventors of the present invention analyzed the expression of SOC1 downstream genes, such as *APETALA*1 (AP1), CAULIFLOWER (CAL), FRUITFULL (FUL), LEAFY (LFY), and *SQUAMOSA* PROMOTER BINDING PROTEIN-LIKE (SPL). All the genes examined were upregulated in the soc1-101D mutant (FIG. 2). In contrast, the expression of AP1, SPL3, and SPL5 was suppressed in the S-K-ox plants, as observed in the soc1-2 mutant. Meanwhile, no cosuppression of endogenous SOC1 gene was observed in the S-K-ox plants (FIG. 2), indicating that the S-K-ox phenotype is caused by overexpression of the S-K gene.

EXAMPLE 2

SOC1 a-siPEPs Inhibit Nuclear Import and DNA Binding of SOC1

Figure 3:
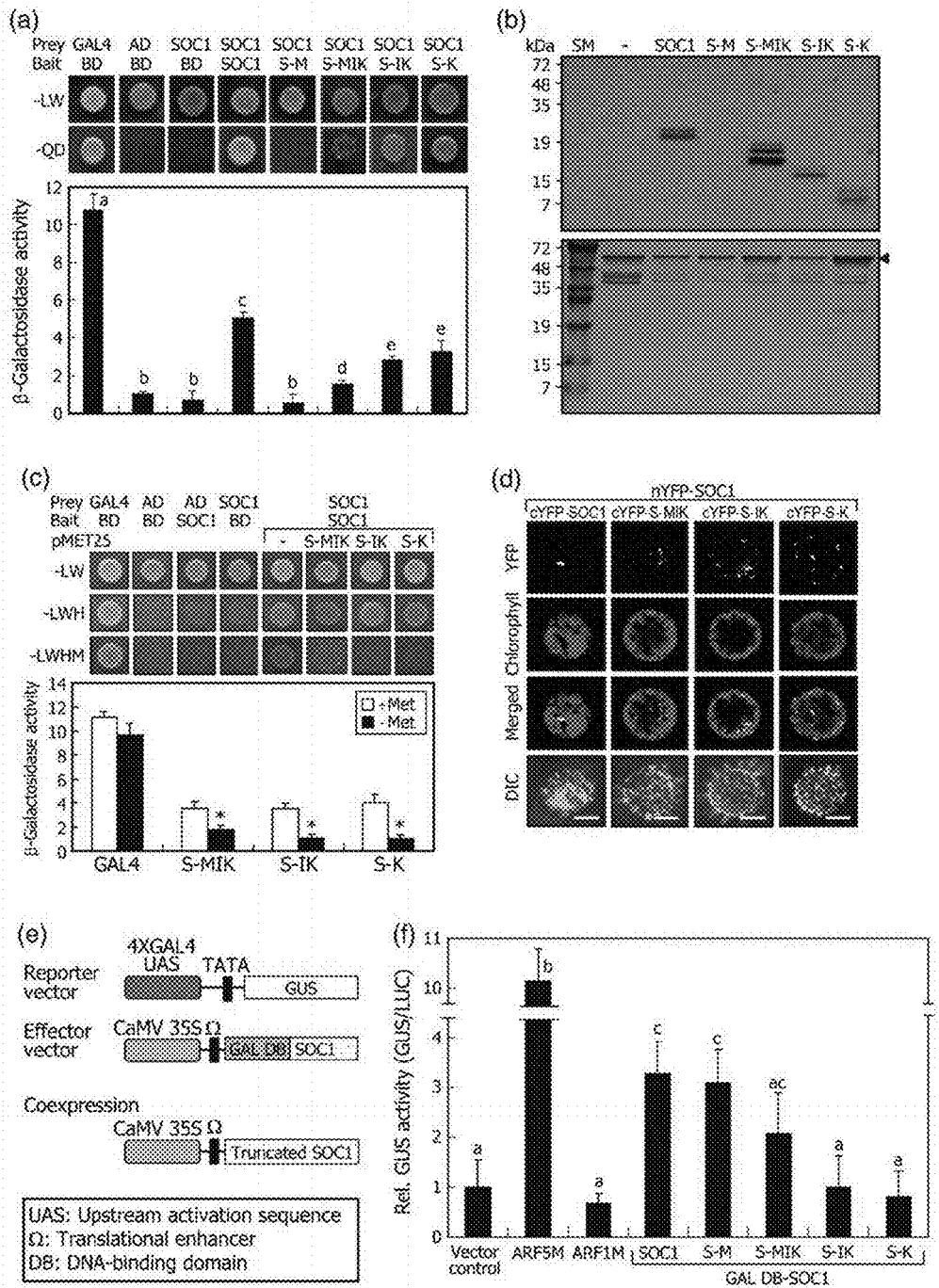
FIG. 3 shows competitive inhibition of SOC1 by a-siPEP.
(a) Interactions of truncated SOC1 proteins with SOC1 in yeast cells. Cell growth on selective media without Leu, Trp, His, and Ade (−QD) represents positive interactions (top panel). Three measurements of β-Gal activities were averaged and statistically treated (bottom panel). Different letters represent significant difference at P<0.05 (one-way ANOVA with Fisher's post hoc test).
(b) in vitro pull-down assays. The maltose binding protein (MBP)-coding sequence was fused in-frame to the 5' end of SOC1 gene, and recombinant MBP-SOC1 fusion protein was prepared in Escherichia coli cells. The $^{35}$S-labeled SOC1 polypeptides were prepared by in vitro translation. Part of Coomassie-stained gel is shown (bottom panel). Arrowhead indicates recombinant MBP-SOC1 protein.
(c) Yeast three-hybrid assays. Truncated SOC1 genes were driven by the methionine (Met)-suppressible promoter (pMET25). AD, activation domain; BD, DNA-binding domain. Note that the truncated SOC1 genes are not expressed on selective media without Leu, Trp, and His (−LWH) but are expressed on selective media without Leu, Trp, His, and Met (−LWHM). Three measurements of β-Gal activities in the presence or absence of Met were averaged and statistically treated (t-test, *P<0.01).
(d) BiFC assays. Partial YFP fusion constructs were transiently expressed in Arabidopsis protoplasts. Scale bars=10 μm.
(e) Reporter and effector vectors used for transient expression assays in Arabidopsis protoplasts.
(f) Effects of truncated SOC1 proteins on transcriptional activity of SOC1. GAL4 transient expression assays were carried out as previously described (Yang et al., Plant Cell, 23, 2155-2168, 2011). ARF5M and ARF1M are transcriptional activator and repressor controls, respectively. Biological triplicates were averaged and statistically treated. Different letters represent significant difference at P<0.05 (one-way ANOVA with Fisher's post hoc test).

It has been known that homo- and heterodimer formations of MADS transcription factors are critical for their binding to target gene promoters (Kaufmann et al., Gene, 347, 183-198, 2005). Inventors of the present invention therefore hypothesized that the truncated SOC1 forms interfere with the SOC1 activity by forming nonfunctional dimers. Yeast-two-hybrid assays revealed that SOC1 forms homodimers (FIG. 3a). It also interacted with the truncated SOC1 forms, such as S-MIK, S-IK, and S-K. in vitro pull-down assays using a recombinant maltose-binding protein-SOC1 (MBP-SOC1) fusion prepared in *E. coli* cells and truncated SOC1 polypeptides, which were produced by in vitro translation, confirmed the formation of SOC1-SOC1 homodimers and heterodimers with the truncated SOC1 forms (FIG. 3b).

Inventors of the present invention next investigated whether the truncated SOC1 forms attenuate the formation of SOC1-SOC1 homodimers. To examine this, the truncated SOC1 proteins were expressed under the control of a methionine (Met)-suppressible promoter in yeast cells. The SOC1 gene was fused in-frame to the gene sequence encoding either the activation domain (AD) or the DNA binding domain (BD) of GAL4, and the AD-SOC1 and BD-SOC1 fusions were coexpressed with the MET25 constructs. AD-SOC1 efficiently interacted with BD-SOC1 in the absence of Met. However, in the presence of Met, yeast cell growth and β-galactosidase activity assays showed that the formation of SOC1-SOC1 homodimers is inhibited by the SOC1 truncated forms, such as the S-K form (FIG. 3c).

It was found that the truncated SOC1 forms, except for S-M that contains nuclear localization signal (Immink et al., Proc. Natl Acad. Sci. USA 99:2416-2421, 2002), are localized mainly in the cytoplasm. Bimolecular fluorescence complementation (BiFC) assays revealed that the heterodimers formed between SOC1 and its truncated forms are detected primarily in the cytoplasm as granular patterns and partially in the nucleus (FIG. 3d), indicating that the truncated forms at least in part sequestrate SOC1 from the nucleus. The spotted distribution of the heterodimers may be due to their association with protein degradation and/or secretion pathways, such as peroxisomes and endoplasmic reticulum. Electrophoretic mobility shift assays (EMSA) showed that the S-K form also attenuates the DNA binding of SOC1, supporting that SOC1 activity is further inhibited in the nucleus. In addition, transient expression assays in *Arabidopsis* protoplasts revealed that the transcriptional activation activity of SOC1 is suppressed by the S-K form (FIGS. 3e, f). These observations indicate that the truncated SOC1 forms suppress the SOC1 activity by sequestrating SOC1 from the nucleus and preventing it from DNA binding.

EXAMPLE 3 a-siPEP-Mediated Inactivation is Also Applicable to AG in *Arabidopsis*

Figure 4:
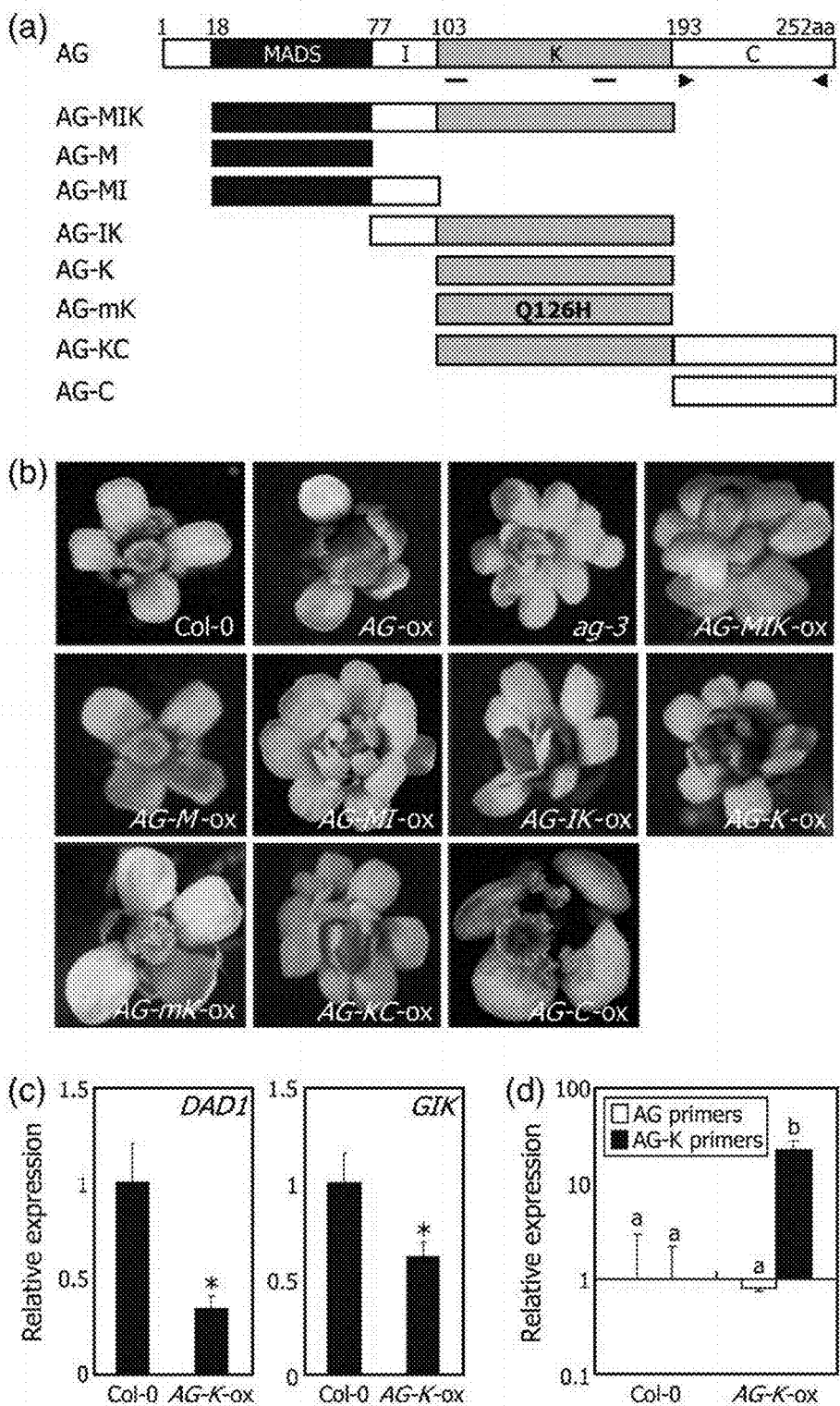
FIG. 4 shows phenotypes of transgenic plants overexpressing different AG gene constructs.
(a) Arabidopsis AG protein constructs used. Numbers indicate residue positions. Q-126, which is essential for AG dimer formation, was mutated to H in the AG-mK construct. Arrowheads and bold bars indicate the positions of AG and AG-K primers used to detect AG and AG-K transcripts, respectively. aa, amino acid.
(b) Floral structures of transgenic Arabidopsis plants overexpressing different AG gene constructs. Fully open flowers of the transgenic Arabidopsis plants were photographed. The AG-deficient ag-3 mutant was included for comparison.
(c) mRNA levels of AG downstream genes. mRNA levels of DAD1 and GIK genes were examined by qRT-PCR. Biological triplicates were averaged and statistically treated using a Student's t-test (*P<0.01). Bars indicate standard error of the mean.
(d) mRNA levels of AG and AG-K genes in Col-0 and AG-K-ox transgenic Arabidopsis plants.
mRNA levels were examined by qRT-PCR using the primer pairs described in (a). Biological triplicates were averaged and statistically treated. Different letters represent significant difference at P<0.05 (one-way ANOVA with Fisher's post hoc test). Bars indicate standard error of the mean. The y-axis was displayed in a logarithmic scale for better comparison of fold changes.

A question was whether the a-siPEP-mediated inactivation is also applicable to other transcription factors. To examine this, inventors of the present invention produced a series of truncated forms of AG transcription factor (FIG. 4a), which plays a role in floral architecture, and they were overproduced in Col-0 plants. Overall phenotypes of the *Arabidopsis* plants overproducing the truncated AG forms were indistinguishable from those of Col-0 plants. Interestingly, the transgenic plants overproducing the truncated AG forms containing K domain displayed disrupted floral structure, as observed in ag-3 knockout mutant (FIG. 4b). In addition, whereas overproduction of AG-K caused abnormal floral structure, that of AG-mK having a point mutation in the K domain and thus being unable to interact with AG had no discernible effects on flower development. These observations support that the negative effects of AG-K on AG occur through protein-protein interactions mediated by the K domain.

To further examine the effects of the AG-K form on flower development, inventors of the present invention analyzed the expression of genes that act downstream of AG gene, including DEFECTIVE IN ANTHER DEHISCENCE 1 (DAD1) and GIANT KILLER (GIK), in the AG-K-ox transgenic plants. The DAD1 and GIK genes were suppressed in the AG-K-ox transgenic plants (FIG. 4c), as has been observed in the ag knockout mutant (Ng et al., PLoS Biol. 7, e1000251, 2009). Expression studies of AG and AG-K genes revealed that there was no cosuppression of endogenous AG gene (FIG. 4d), indicating that the disrupted floral architecture in the AG-K-ox transgenic plants is due to overproduction of the AG-K form, similar to the roles played by the SOC1-specific a-siPEPs.

EXAMPLE 4 a-siPEP Tool can be Applied to *Brachypodium*

Figure 5:
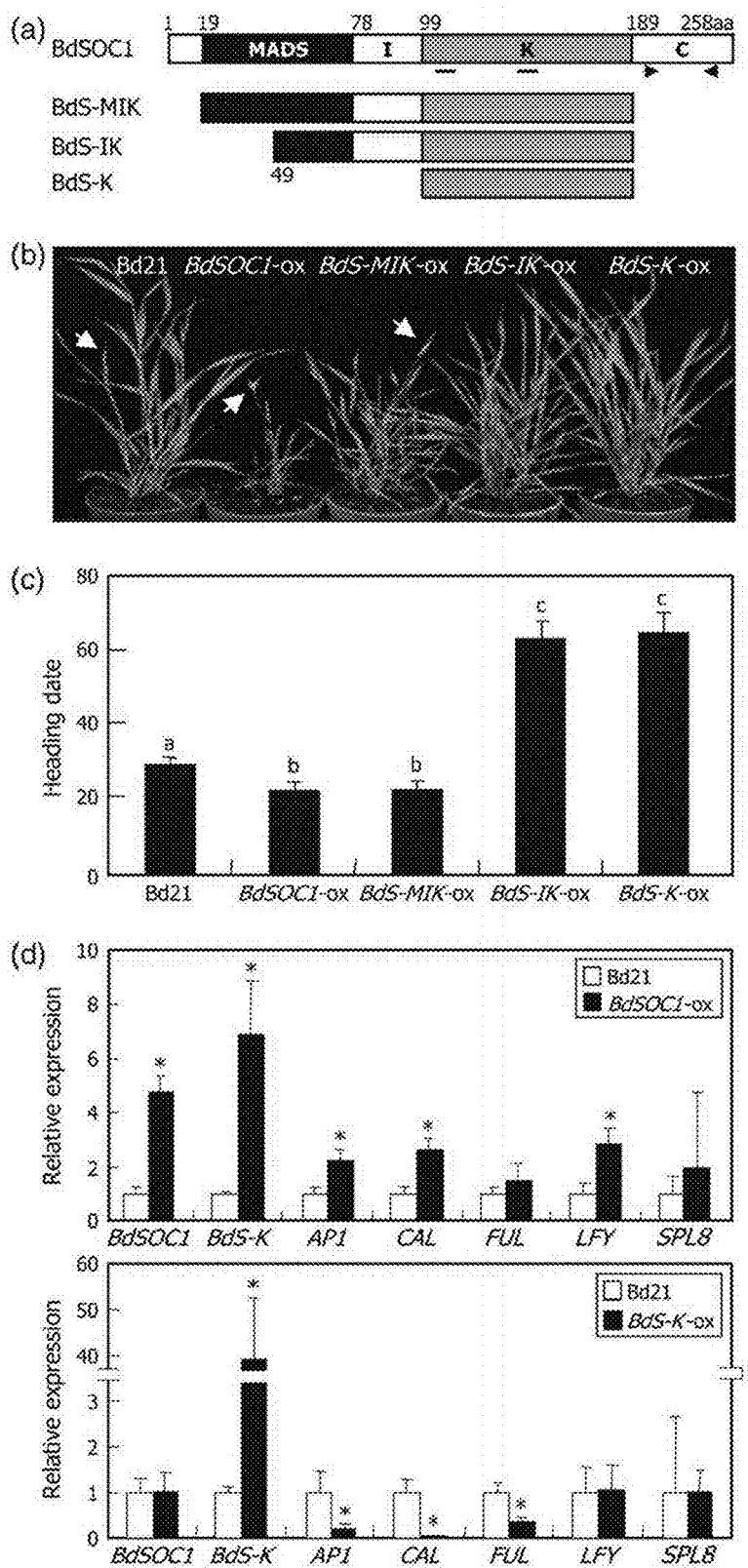
FIG. 5 shows targeted inactivation of BdSOC1 by a-siPEPs in *Brachypodium* flowering.

Inventors of the present invention next examined the feasibility of a-siPEP tool in the monocot model *Brachypodium*, which is widely used as a model system for biofuel grass studies. A putative *Brachypodium* SOC1 protein (BdSOC1) was identified by amino acid sequence analysis and protein domain prediction (FIG. 5a). Genes encoding several truncated forms of BdSOC1 were transformed into *Brachypodium* plants. The transgenic *Brachypodium* plants overproducing the truncated BdSOC1 forms exhibited delayed heading (FIGS. 5b, c), as was observed with the transgenic *Arabidopsis* plants overproducing truncated SOC1 forms. The delayed flowering was most prominent in the BdS-K-ox transgenic plants that overproduce the K domain. Consistent with the delayed flowering, the expression of BdSOC1 downstream genes, such as AP1, CAL, and FUL, was elevated in the BdSOC1-ox plants but suppressed in the BdS-K-ox plants (FIG. 5d).

in vitro pull down assays using recombinant MBP-BdSOC1 proteins produced in *E. coli* cells and truncated BdSOC1 polypeptides, which were prepared by in vitro translation, showed that BdSOC1 interacted with itself and the truncated forms, such as BdS-MIK, BdS-IK, and BdS-K (FIG. 6a). The truncated forms were localized mostly in the cytoplasm, and heterodimers were detected mainly in the cytoplasm and partially in the nucleus (FIG. 6b), as observed with a-siPEPs of *Arabidopsis* SOC1. Inventors of the present invention speculated that the a-siPEPs can also prevent binding of the BdSOC1 protein to target DNA. These results indicate that the truncated BdSOC1 forms inactivate the BdSOC1 activity in a manner similar to what played by the truncated SOC1 forms in *Arabidopsis* flowering.

EXAMPLE 5 a-siPEP Inactivates LHY Transcription Factor in Circadian Clock Control

Many transcription factors are targeted by genomic siPEPs. Inventors of the present invention found that a-siPEPs inactivate two MADS box transcription factors, SOC1 and AG, in *Arabidopsis* and *Brachypodium*.

To examine whether the a-siPEP tool is also applicable to other transcription factors, inventors of the present invention designed an a-siPEP of LHY, a MYB transcription factor that is involved in circadian clock control. The LHY transcription factor has putative dimerization domain (DD) consisting of 260 residues (FIG. 7a), which is critical for interactions with CIRCADIAN CLOCK-ASSOCIATED 1 (CCA1) in maintaining circadian rhythm oscillation (Lu et al., Plant Physiol. 150, 834-843, 2009). Gene sequence encoding the LHY-DD domain was transformed into Col-0 plant, resulting in LHY-DD-ox transgenic plants.

lhy loss-of-function mutants are phenotypically indistinguishable from wild-type plants but display disturbed circadian rhythms (Mizoguchi et al., Dev. Cell, 2, 629-641, 2002). Notably, it was found that the periods of circadian oscillations were shortened in the LHY-DD-ox transgenic plants (FIG. 7b), as has been observed in the LHY-deficient mutants.

Dynamic formation of LHY-LHY and CCA1-CCA1 homodimers and CCA1-LHY heterodimers plays a critical role in the clock function, and circadian rhythms are severely altered in cca1 lhy double mutants (Lu et al., Plant Physiol. 150, 834-843, 2009). Inventors of the present invention found that the rhythmicity of TOC1 gene expression was altered mildly in CCA1-deficient cca1-2 mutant, as observed in the LHY-DD-ox transgenic plants, which is probably because LHY DD inhibits LHY-LHY and CCA1-LHY interactions but does not influence CCA1-CCA1 interactions. These observations indicate that the a-siPEP tool is also relevant to the MYB transcription factor LHY, further supporting its broad utility in targeting diverse transcription factor members.

Inventors of the present invention here demonstrate that a-siPEPs that structurally mimic genomic siPEPs efficiently inactivate a variety of transcription factors in *Arabidopsis* and *Brachypodium* by attenuating nuclear localization and DNA binding of the target transcription factors (FIG. 8). Our data strongly support that the a-siPEP tool is readily applicable to both monocot and dicot plants.

The invention claimed is:

1. A recombinant plant vector comprising a gene encoding an artificial small interfering peptide (a-siPEP), wherein the artificial small interfering peptide is a truncated form of a plant transcription factor, wherein the plant transcription factor has the amino acid sequence selected from the group consisting of SEQ ID NO:1, SEQ ID NO:2, and SEQ ID NO:3,
with a proviso that:
(i) a dimerization domain of the plant transcription factor is included in the truncated form: and
(ii) the artificial small interfering peptide comprises amino acids 82-170 of SEQ ID NO:1 when the plant transcription factor has the amino acid sequence of SEQ ID NO:1;
the artificial small interfering peptide comprises amino acids 99-188 of SEQ ID NO:2 when the plant transcription factor has the amino acid sequence of SEQ ID NO:2; and
the artificial small interfering peptide comprises amino acids 103-192 of SEQ ID NO:3 when the plant transcription factor has the amino acid sequence of SEQ ID NO:3, wherein a plant transformed with said vector exhibits a delayed flowering phenotype.

2. A plant transformed with the recombinant plant vector described claim 1 to inhibit transcription factor activity.

3. A method for inhibiting transcription factor activity of a plant comprising transforming a plant cell with the recombinant vector of claim 1 to overexpress the gene encoding the artificial small interfering peptide.

4. A method for producing a transgenic plant with inhibited transcription factor activity comprising transforming a plant cell with the recombinant vector of claim 1 to overexpress the gene encoding the artificial small interfering peptide.

5. A transgenic plant having inhibited transcription factor activity which is produced by the method described in claim 4.

6. The transgenic plant according to claim 5, characterized in that the plant is either a dicot plant or a monocot plant.

7. The transgenic plant according to claim 5, characterized in that the plant is either *Arabidopsis thaliana* or *Brachypodium distachyon*.

8. A transgenic seed of the transgenic plant described in claim 5, wherein the transgenic seed comprises said recombinant vector.

9. A composition for inhibiting transcription factor activity of a plant which comprises the recombinant plant vector of claim 1.

10. The recombinant vector of claim 1, wherein the plant transcription factor has the amino acid sequence of SEQ ID NO: 1, and a plant transformed with the with the recombinant vector exhibits a delayed flowering phenotype.

* * * * *

SEQUENCE LISTING

```
<160> NUMBER OF SEQ ID NOS: 118

<210> SEQ ID NO 1
<211> LENGTH: 214
<212> TYPE: PRT
<213> ORGANISM: Arabidopsis thaliana

<400> SEQUENCE: 1

Met Val Arg Gly Lys Thr Gln Met Lys Arg Ile Glu Asn Ala Thr Ser
1               5                   10                  15
```

Arg Gln Val Thr Phe Ser Lys Arg Asn Gly Leu Leu Lys Ala
            20                  25                  30

Phe Glu Leu Ser Val Leu Cys Asp Ala Glu Val Ser Leu Ile Ile Phe
            35                  40                  45

Ser Pro Lys Gly Lys Leu Tyr Glu Phe Ala Ser Ser Asn Met Gln Asp
 50                  55                  60

Thr Ile Asp Arg Tyr Leu Arg His Thr Lys Asp Arg Val Ser Thr Lys
65                  70                  75                  80

Pro Val Ser Glu Glu Asn Met Gln His Leu Lys Tyr Glu Ala Ala Asn
                85                  90                  95

Met Met Lys Lys Ile Glu Gln Leu Glu Ala Ser Lys Arg Lys Leu Leu
            100                 105                 110

Gly Glu Gly Ile Gly Thr Cys Ser Ile Glu Glu Leu Gln Gln Ile Glu
            115                 120                 125

Gln Gln Leu Glu Lys Ser Val Lys Cys Ile Arg Ala Arg Lys Thr Gln
130                 135                 140

Val Phe Lys Glu Gln Ile Glu Gln Leu Lys Gln Lys Lys Ala Leu
145                 150                 155                 160

Ala Ala Glu Asn Glu Lys Leu Ser Glu Lys Trp Gly Ser His Glu Ser
                165                 170                 175

Glu Val Trp Ser Asn Lys Asn Gln Glu Ser Thr Gly Arg Gly Asp Glu
            180                 185                 190

Glu Ser Ser Pro Ser Ser Glu Val Glu Thr Gln Leu Phe Ile Gly Leu
            195                 200                 205

Pro Cys Ser Ser Arg Lys
            210

<210> SEQ ID NO 2
<211> LENGTH: 258
<212> TYPE: PRT
<213> ORGANISM: Brachypodium distachyon

<400> SEQUENCE: 2

Met Gln Ala Gly Arg Leu Asp Arg Arg Gly Ser Ile Trp Asp Arg Ser
1               5                   10                  15

Thr Lys Met Val Arg Gly Lys Thr Gln Leu Lys Arg Ile Glu Asn Arg
            20                  25                  30

Ala Ser Arg Gln Val Thr Phe Ser Lys Arg Arg Gly Gly Leu Arg Lys
            35                  40                  45

Lys Ala His Glu Leu Ser Val Leu Cys Asp Val Glu Val Ala Leu Ile
 50                  55                  60

Val Phe Ser Pro Ser Gly Arg Leu Tyr Glu Phe Ala Ser Ala Ser Met
65                  70                  75                  80

Gln Lys Thr Leu Glu Arg Tyr Lys Ala Ser Thr Lys Asp Lys Thr Ser
                85                  90                  95

Ser Pro Thr Ala Gln Gln Asp Ile Glu Lys Ile Lys Ala Asp Ala Glu
            100                 105                 110

Gly Leu Ser Gln Lys Leu Glu Ala Leu Glu Ala Tyr Arg Arg Lys Phe
            115                 120                 125

Leu Gly Glu Lys Leu Glu Asp Cys Ser Phe Glu Glu Leu Asn Ser
130                 135                 140

Leu Glu Val Lys Met Glu Lys Ser Leu Arg Ser Ile Arg Arg Met Lys
145                 150                 155                 160

Thr Gln Val Phe Glu Asp Gln Leu Ala Lys Leu Arg Gln Lys Glu Met
                165                 170                 175

```
Thr Leu Arg Lys Glu Asn Glu Asp Leu Arg Gly Lys Val Thr Lys Gly
            180                 185                 190

Ser Glu Asn Glu Asp Leu Gln Ala Lys Cys Lys Asp Val Val Asp Leu
            195                 200                 205

Thr Leu Val Thr Ser Ala Pro Met Ile Ala Ala Ala Ala Ala Ala Glu
            210                 215                 220

Glu Glu Glu Glu Asn Pro Pro Glu Ala Gln Pro Glu Leu Asn Lys Asp
225                 230                 235                 240

Ala Met Asp Val Glu Thr Glu Leu Phe Ile Gly Leu Pro Gly Arg Asn
                245                 250                 255

Arg Ser

<210> SEQ ID NO 3
<211> LENGTH: 252
<212> TYPE: PRT
<213> ORGANISM: Arabidopsis thaliana

<400> SEQUENCE: 3

Thr Ala Tyr Gln Ser Glu Leu Gly Gly Asp Ser Ser Pro Leu Arg Lys
1               5                   10                  15

Ser Gly Arg Gly Lys Ile Glu Ile Lys Arg Ile Glu Asn Thr Thr Asn
            20                  25                  30

Arg Gln Val Thr Phe Cys Lys Arg Arg Asn Gly Leu Leu Lys Lys Ala
            35                  40                  45

Tyr Glu Leu Ser Val Leu Cys Asp Ala Glu Val Ala Leu Ile Val Phe
        50                  55                  60

Ser Ser Arg Gly Arg Leu Tyr Glu Tyr Ser Asn Asn Ser Val Lys Gly
65                  70                  75                  80

Thr Ile Glu Arg Tyr Lys Lys Ala Ile Ser Asp Asn Ser Asn Thr Gly
                85                  90                  95

Ser Val Ala Glu Ile Asn Ala Gln Tyr Tyr Gln Gln Glu Ser Ala Lys
            100                 105                 110

Leu Arg Gln Gln Ile Ile Ser Ile Gln Asn Ser Asn Arg Gln Leu Met
            115                 120                 125

Gly Glu Thr Ile Gly Ser Met Ser Pro Lys Glu Leu Arg Asn Leu Glu
            130                 135                 140

Gly Arg Leu Glu Arg Ser Ile Thr Arg Ile Arg Ser Lys Lys Asn Glu
145                 150                 155                 160

Leu Leu Phe Ser Glu Ile Asp Tyr Met Gln Lys Arg Glu Val Asp Leu
                165                 170                 175

His Asn Asp Asn Gln Ile Leu Arg Ala Lys Ile Ala Glu Asn Glu Arg
            180                 185                 190

Asn Asn Pro Ser Ile Ser Leu Met Pro Gly Gly Ser Asn Tyr Glu Gln
            195                 200                 205

Leu Met Pro Pro Pro Gln Thr Gln Ser Gln Pro Phe Asp Ser Arg Asn
            210                 215                 220

Tyr Phe Gln Val Ala Ala Leu Gln Pro Asn Asn His His Tyr Ser Ser
225                 230                 235                 240

Ala Gly Arg Gln Asp Gln Thr Ala Leu Gln Leu Val
                245                 250

<210> SEQ ID NO 4
<211> LENGTH: 645
<212> TYPE: PRT
<213> ORGANISM: Arabidopsis thaliana
```

<400> SEQUENCE: 4

```
Met Asp Thr Asn Thr Ser Gly Glu Glu Leu Leu Ala Lys Ala Arg Lys
1               5                   10                  15

Pro Tyr Thr Ile Thr Lys Gln Arg Glu Arg Trp Thr Glu Asp Glu His
            20                  25                  30

Glu Arg Phe Leu Glu Ala Leu Arg Leu Tyr Gly Arg Ala Trp Gln Arg
        35                  40                  45

Ile Glu Glu His Ile Gly Thr Lys Thr Ala Val Gln Ile Arg Ser His
    50                  55                  60

Ala Gln Lys Phe Phe Thr Lys Leu Glu Lys Glu Ala Glu Val Lys Gly
65                  70                  75                  80

Ile Pro Val Cys Gln Ala Leu Asp Ile Glu Ile Pro Pro Arg Pro
                85                  90                  95

Lys Arg Lys Pro Asn Thr Pro Tyr Pro Arg Lys Pro Gly Asn Asn Gly
            100                 105                 110

Thr Ser Ser Ser Gln Val Ser Ser Ala Lys Asp Ala Lys Leu Val Ser
            115                 120                 125

Ser Ala Ser Ser Ser Gln Leu Asn Gln Ala Phe Leu Asp Leu Glu Lys
130                 135                 140

Met Pro Phe Ser Glu Lys Thr Ser Thr Gly Lys Glu Asn Gln Asp Glu
145                 150                 155                 160

Asn Cys Ser Gly Val Ser Thr Val Asn Lys Tyr Pro Leu Pro Thr Lys
                165                 170                 175

Gln Val Ser Gly Asp Ile Glu Thr Ser Lys Thr Ser Thr Val Asp Asn
            180                 185                 190

Ala Val Gln Asp Val Pro Lys Lys Asn Lys Asp Lys Asp Gly Asn Asp
            195                 200                 205

Gly Thr Thr Val His Ser Met Gln Asn Tyr Pro Trp His Phe His Ala
        210                 215                 220

Asp Ile Val Asn Gly Asn Ile Ala Lys Cys Pro Gln Asn His Pro Ser
225                 230                 235                 240

Gly Met Val Ser Gln Asp Phe Met Phe His Pro Met Arg Glu Glu Thr
                245                 250                 255

His Gly His Ala Asn Leu Gln Ala Thr Thr Ala Ser Ala Thr Thr Thr
            260                 265                 270

Ala Ser His Gln Ala Phe Pro Ala Cys His Ser Gln Asp Asp Tyr Arg
            275                 280                 285

Ser Phe Leu Gln Ile Ser Ser Thr Phe Ser Asn Leu Ile Met Ser Thr
        290                 295                 300

Leu Leu Gln Asn Pro Ala Ala His Ala Ala Thr Phe Ala Ala Ser
305                 310                 315                 320

Val Trp Pro Tyr Ala Ser Val Gly Asn Ser Gly Asp Ser Ser Thr Pro
                325                 330                 335

Met Ser Ser Pro Pro Ser Ile Thr Ala Ile Ala Ala Thr Val
            340                 345                 350

Ala Ala Ala Thr Ala Trp Trp Ala Ser His Gly Leu Leu Pro Val Cys
            355                 360                 365

Ala Pro Ala Pro Ile Thr Cys Val Pro Phe Ser Thr Val Ala Val Pro
        370                 375                 380

Thr Pro Ala Met Thr Glu Met Asp Thr Val Glu Asn Thr Gln Pro Phe
385                 390                 395                 400

Glu Lys Gln Asn Thr Ala Leu Gln Asp Gln Asn Leu Ala Ser Lys Ser
```

```
                    405                 410                 415
Pro Ala Ser Ser Ser Asp Asp Ser Asp Glu Thr Gly Val Thr Lys Leu
            420                 425                 430

Asn Ala Asp Ser Lys Thr Asn Asp Asp Lys Ile Glu Glu Val Val Val
            435                 440                 445

Thr Ala Ala Val His Asp Ser Asn Thr Ala Gln Lys Lys Asn Leu Val
            450                 455                 460

Asp Arg Ser Ser Cys Gly Ser Asn Thr Pro Ser Gly Ser Asp Ala Glu
465                 470                 475                 480

Thr Asp Ala Leu Asp Lys Met Glu Lys Asp Lys Glu Asp Val Lys Glu
                485                 490                 495

Thr Asp Glu Asn Gln Pro Asp Val Ile Glu Leu Asn Asn Arg Lys Ile
            500                 505                 510

Lys Met Arg Asp Asn Asn Ser Asn Asn Asn Ala Thr Thr Asp Ser Trp
            515                 520                 525

Lys Glu Val Ser Glu Glu Gly Arg Ile Ala Phe Gln Ala Leu Phe Ala
            530                 535                 540

Arg Glu Arg Leu Pro Gln Ser Phe Ser Pro Gln Val Ala Glu Asn
545                 550                 555                 560

Val Asn Arg Lys Gln Ser Asp Thr Ser Met Pro Leu Ala Pro Asn Phe
                565                 570                 575

Lys Ser Gln Asp Ser Cys Ala Ala Asp Gln Glu Gly Val Met Ile
            580                 585                 590

Gly Val Gly Thr Cys Lys Ser Leu Lys Thr Arg Gln Thr Gly Phe Lys
            595                 600                 605

Pro Tyr Lys Arg Cys Ser Met Glu Val Lys Glu Ser Gln Val Gly Asn
            610                 615                 620

Ile Asn Asn Gln Ser Asp Glu Lys Val Cys Lys Arg Leu Arg Leu Glu
625                 630                 635                 640

Gly Glu Ala Ser Thr
            645

<210> SEQ ID NO 5
<211> LENGTH: 645
<212> TYPE: DNA
<213> ORGANISM: Arabidopsis thaliana

<400> SEQUENCE: 5
atggtgaggg gcaaaactca gatgaagaga atagagaatg caacaagcag acaagtgact      60
ttctccaaaa gaaggaatgg tttgttgaag aaagcctttg agctctcagt gctttgtgat     120
gctgaagttt ctcttatcat cttctctcct aaaggcaaac tttatgaatt cgccagctcc     180
aatatgcaag ataccataga tcgttatctg aggcatacta aggatcgagt cagcaccaaa     240
ccggtttctg aagaaaatat gcagcatttg aaatatgaag cagcaaacat gatgaagaaa     300
attgaacaac tcgaagcttc taaacgtaaa ctcttgggag aaggcatagg aacatgctca     360
atcgaggagc tgcaacagat tgagcaacag cttgagaaaa gtgtcaaatg tattcgagca     420
agaaagactc aagtgtttaa ggaacaaatt gagcagctca agcaaaagga gaaagctcta     480
gctgcagaaa acgagaagct ctctgaaaag tgggatctc atgaaagcga gtttggtca      540 aataagaatc aagaaagtac tggaagaggt gatgaagaga gtagcccaag ttctgaagta     600
gagacgcaat tgttcattgg gttaccttgt tcttcaagaa agtga                    645

<210> SEQ ID NO 6
```

```
<211> LENGTH: 777
<212> TYPE: DNA
<213> ORGANISM: Brachypodium distachyon

<400> SEQUENCE: 6
atgcaggcag gccggctcga tcggagagga tctatttggg atcggtcgac gaagatggtg      60 cggggggaaga cgcagctgaa gcggattgag aaccgggcga gccggcaggt gaccttctcc     120
aagcgccgcg gcgggctgcg caagaaggcg cacgagctct ccgtcctctg cgatgttgag     180
gtcgccctca tcgtcttctc ccccagcggc cgcctctacg agttcgccag cgccagcatg     240
cagaaaacac tagaacgtta taaggcatcc acaaaggaca aaactagcag cccaacggca     300
cagcaagaca tagagaagat aaaagctgat gctgagggct tgtcacagaa actggaagct     360
cttgaagcct acagaaggaa attttttggg gaaaagttgg aagacgactg ttcttttgaa     420
gagctgaata gtctggaggt caagatggaa aagagccttc gtagcatcag gagaatgaag     480
actcaggtgt ttgaagatca gctcgctaag ctgagacaga aggagatgac gttgcgcaag     540
gagaacgaag atctaagggg caaggtgacc aaaggcagcg aaaacgaaga tcttcaggcc     600
aagtgcaagg atgtggtcga ccttacgctg gtgacctctg ctcccatgat cgccgcggcg     660
gcggcggcga aggaggagga ggagaaccct cctgaggctc agccggagct gaacaaggac     720
gccatggacg tggagacgga gctgttcatc ggactgcccg cagaaatcg ctcttga         777

<210> SEQ ID NO 7
<211> LENGTH: 759
<212> TYPE: DNA
<213> ORGANISM: Arabidopsis thaliana

<400> SEQUENCE: 7
acggcgtacc aatcggagct aggaggagat tcctctccct tgaggaaatc tgggagagga      60
aagatcgaaa tcaaacggat cgagaacaca acgaatcgtc aagtcacttt ttgcaaacgt     120
agaaatggtt tgctcaagaa agcttacgag ctctctgttc tttgtgatgc tgaagtcgca     180
ctcatcgtct tctctagccg tggtcgtctc tatgagtact ctaacaacag tgtaaaaggg     240
actattgaga ggtacaagaa ggcaatatcg gacaattcta acaccggatc ggtggcagaa     300
attaatgcac agtattatca acaagaatca gccaaattgc gtcaacaaat aatcagcata     360
caaaactcca caggcaattt gatgggtgag acgatagggt caatgtctcc caaagagctc     420
aggaacttgg aaggcagatt agagagaagt attacccgaa tccgatccaa gaagaatgag     480
ctcttatttt ctgaaatcga ctacatgcag aaaagagaag ttgatttgca taacgataac     540
cagattcttc gtgcaaagat agctgaaaat gagaggaaca atccgagtat aagtctaatg     600
ccaggaggat ctaactacga gcagcttatg ccaccacctc aaacgcaatc tcaaccgttt     660
gattcacgga attatttcca gtcgcggca ttgcaaccta caatcacca ttactcatcc      720 gcgggtcgcc aagaccaaac cgctctccag ttagtgtaa                            759

<210> SEQ ID NO 8
<211> LENGTH: 1938
<212> TYPE: DNA
<213> ORGANISM: Arabidopsis thaliana

<400> SEQUENCE: 8
atggatacta atacatctgg agaagaatta ttagctaagg caagaaagcc atatacaata      60
acaaagcagc gagagcgatg gactgaggat gagcatgaga ggtttctaga agccttgagg     120 cttatatggaa gagcttggca acgaattgaa gaacatattg ggacaaagac tgctgttcag     180
```

```
atcagaagtc atgcacaaaa gttcttcaca aagttggaga aagaggctga agttaaaggc    240
atccctgttt gccaagcttt ggacatagaa attccgcctc ctcgtcctaa acgaaaaccc    300
aatactcctt atcctcgaaa gcctgggaac aacggtacat cttcctctca agtatcatca    360
gcaaaagatg caaaacttgt ttcatcggcc tcttcttcac agttgaatca ggcgttcttg    420
gatttggaaa aaatgccgtt ctctgagaaa acatcaactg gaaaagaaaa tcaagatgag    480
aattgctcgg gtgtttctac tgtgaacaag tatcccttac caacgaaaca ggtaagtggc    540
gacattgaaa caagtaagac ctcaactgtg gacaacgcgg ttcaagatgt tcccaagaag    600
aacaaagaca aagatggtaa cgatggtact actgtgcaca gcatgcaaaa ctacccttgg    660
catttccacg cagatattgt gaacgggaat atagcaaaat gccctcaaaa tcatccctca    720
ggtatggtat ctcaagactt catgtttcat cctatgagag aagaaactca cgggcacgca    780
aatcttcaag ctacaacagc atctgctact actacagctt ctcatcaagc gtttccagct    840
tgtcattcac aggatgatta ccgttcgttt ctccagatat catctacttt ctccaatctt    900
attatgtcaa ctctcctaca gaatcctgca gctcatgctg cagctacatt cgctgcttcg    960
gtctggcctt atgcgagtgt cgggaattct ggtgattcat caaccccaat gagctcttct   1020
cctccaagta taactgccat tgccgctgct acagtagctg ctgcaactgc ttggtgggct   1080
tctcatggac ttcttcctgt atgcgctcca gctccaataa catgtgttcc attctcaact   1140
gttgcagttc caactccagc aatgactgaa atggataccg ttgaaaatac tcaaccgttt   1200
gagaaacaaa acacagctct gcaagatcaa aacttggctt cgaaatctcc agcttcatca   1260
tctgatgatt cagatgagac tggagtaacc aagctaaatg ccgactcaaa aaccaatgat   1320
gataaaattg aggaggttgt tgttactgcc gctgtgcatg actcaaacac tgcccagaag   1380
aaaaatcttg tggaccgctc atcctgtggc tcaaatacac cttcagggag tgacgcagaa   1440
actgatgcat tagataaaat ggagaaagat aaagaggatg tgaaggagac agatgagaat   1500
cagccagatg ttattgagtt aaataaccgt aagattaaaa tgagagacaa caacagcaac   1560
aacaatgcaa ctactgattc gtggaaggaa gtctccgaag agggtcgtat agcgtttcag   1620
gctctctttg caagagaaag attgcctcaa agcttttcgc ctcctcaagt ggcagagaat   1680
gtgaatagaa aacaaagtga cacgtcaatg ccattggctc ctaatttcaa agccaggat   1740 tcttgtgctg cagaccaaga aggagtagta atgatcggtg ttggaacatg caagagtctt   1800
aaaacgagac agacaggatt taagccatac aagagatgtt caatggaagt gaaagagagc   1860
caagtgggaa acataaacaa tcaaagtgat gaaaaagtct gcaaaaggct tcgattggaa   1920
ggagaagctt ctacatga                                                  1938
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9

```
tgaccacaca gtctctgcaa                                                  20
```

<210> SEQ ID NO 10
<211> LENGTH: 20
<212> TYPE: DNA
<213> ORGANISM: Artificial Sequence
<220> FEATURE:

<223> OTHER INFORMATION: Primer

<400> SEQUENCE: 10
accagggaga cttgttggac                                               20

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ggatctcatg aaagcgaagt tt                                            22

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
tcactttctt gaagaacaag gta                                           23

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
aagaaaatat gcagcatttg aaata                                         25

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
cctatgcctt ctcccaagag t                                             21

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
tgatgctgaa gttgctcttg tt                                            22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
cgaccagttt gtattgacgt cg                                            22

```
<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gggaaggggt agggttgaat                                        20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
acaataaggg aaacctcggc                                        20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
atgatggaac tccgttgtcg                                        20

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
ttcatgagaa atcattacca agatatg                                27

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
ttactgggac gcaggtcaag                                        20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cccaaaccac tacctccgtt                                        20

<210> SEQ ID NO 23
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 23
acaatgcagc aggtttcacg                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cttttccgcc ttctctcgtt                                              20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gatcagataa accctcccgc                                              20

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
accatgacca acttttcttg aca                                          23

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
cgccgtaaat gtcaccaatc                                              20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gaagacgctg tcgtttggaa                                              20

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
tcaaccgttt gattcacgg                                               19

<210> SEQ ID NO 30
<211> LENGTH: 23
```

<212> TYPE: DNA
<213> ORGANISM: Artificial Sequence
<220> FEATURE:
<223> OTHER INFORMATION: Primer

<400> SEQUENCE: 30
ttacactaac tggagagcgg ttt                                    23

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ctcaggaact tggaaggcag                                        20

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
atcaacttct cttttctgca tgtagt                                 26

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ttcgtgccac gtcaggtatt                                        20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
tctttgtcct ggcaaactgc                                        20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gtaatggtca tggcagcgtc                                        20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36

-continued acatattccc tccacctccg                                               20

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
tcttcgcaga atccctgtga t                                             21

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gctgcaccta gcttcaagca                                               20

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
aaaaagcagg ctctatggtg aggggcaaaa ct                                 32

<210> SEQ ID NO 40
<211> LENGTH: 34
<212> TYPE: DNA
<213> ORGANISM: Artificial Sequence
<220> FEATURE:
<223> OTHER INFORMATION: Primer

<400> SEQUENCE: 40
agaaagctgg gtttcaggag ctggcgaatt cata                               34

<210> SEQ ID NO 41
<211> LENGTH: 32
<212> TYPE: DNA
<213> ORGANISM: Artificial Sequence
<220> FEATURE:
<223> OTHER INFORMATION: Primer

<400> SEQUENCE: 41
aaaaagcagg ctctatggtg aggggcaaaa ct                                 32

<210> SEQ ID NO 42
<211> LENGTH: 38
<212> TYPE: DNA
<213> ORGANISM: Artificial Sequence
<220> FEATURE:
<223> OTHER INFORMATION: Primer

<400> SEQUENCE: 42
aaaaagcagg ctctatgaag aaagcctttg agctctca                           38

<210> SEQ ID NO 43
<211> LENGTH: 39
<212> TYPE: DNA
<213> ORGANISM: Artificial Sequence -continued

```
<220> FEATURE:
<223> OTHER INFORMATION: Primer

<400> SEQUENCE: 43
aaaaagcagg ctctatggtt tctgaagaaa atatgcagc                                39

<210> SEQ ID NO 44
<211> LENGTH: 37
<212> TYPE: DNA
<213> ORGANISM: Artificial Sequence
<220> FEATURE:
<223> OTHER INFORMATION: Primer

<400> SEQUENCE: 44
agaaagctgg gtttcaccac ttttcagaga gcttctc                                  37

<210> SEQ ID NO 45
<211> LENGTH: 33
<212> TYPE: DNA
<213> ORGANISM: Artificial Sequence
<220> FEATURE:
<223> OTHER INFORMATION: Primer

<400> SEQUENCE: 45
aaaaagcagg ctctatgacg gcgtaccaat cgg                                      33

<210> SEQ ID NO 46
<211> LENGTH: 34
<212> TYPE: DNA
<213> ORGANISM: Artificial Sequence
<220> FEATURE:
<223> OTHER INFORMATION: Primer

<400> SEQUENCE: 46
agaaagctgg gttttacact aactggagag cggt                                     34

<210> SEQ ID NO 47
<211> LENGTH: 44
<212> TYPE: DNA
<213> ORGANISM: Artificial Sequence
<220> FEATURE:
<223> OTHER INFORMATION: Primer

<400> SEQUENCE: 47
aaaaagcagg ctctatgggg agaggaaaga tcgaaatcaa acgg                          44

<210> SEQ ID NO 48
<211> LENGTH: 46
<212> TYPE: DNA
<213> ORGANISM: Artificial Sequence
<220> FEATURE:
<223> OTHER INFORMATION: Primer

<400> SEQUENCE: 48
agaaagctgg gttttagttg ttagagtact catagagacg accacg                        46

<210> SEQ ID NO 49
<211> LENGTH: 42
<212> TYPE: DNA
<213> ORGANISM: Artificial Sequence
<220> FEATURE:
<223> OTHER INFORMATION: Primer

<400> SEQUENCE: 49
aaaaagcagg ctctatgagt gtaaaaggga ctattgagag gt                            42
```

```
<210> SEQ ID NO 50
<211> LENGTH: 43
<212> TYPE: DNA
<213> ORGANISM: Artificial Sequence
<220> FEATURE:
<223> OTHER INFORMATION: Primer

<400> SEQUENCE: 50
agaaagctgg gttttagtcc gatattgcct tcttgtacct ctc          43

<210> SEQ ID NO 51
<211> LENGTH: 44
<212> TYPE: DNA
<213> ORGANISM: Artificial Sequence
<220> FEATURE:
<223> OTHER INFORMATION: Primer

<400> SEQUENCE: 51
aaaaagcagg ctctatgaat ctaacaccg gatcggtggc agaa          44

<210> SEQ ID NO 52
<211> LENGTH: 49
<212> TYPE: DNA
<213> ORGANISM: Artificial Sequence
<220> FEATURE:
<223> OTHER INFORMATION: Primer

<400> SEQUENCE: 52
agaaagctgg gttttaatca acttctcttt tctgcatgta gtcgatttc    49

<210> SEQ ID NO 53
<211> LENGTH: 42
<212> TYPE: DNA
<213> ORGANISM: Artificial Sequence
<220> FEATURE:
<223> OTHER INFORMATION: Primer

<400> SEQUENCE: 53
aaaaagcagg ctctatgttg cataacgata accagattct tc           42

<210> SEQ ID NO 54
<211> LENGTH: 42
<212> TYPE: DNA
<213> ORGANISM: Artificial Sequence
<220> FEATURE:
<223> OTHER INFORMATION: Primer

<400> SEQUENCE: 54
aaaaagcagg ctctatgaat actccttatc ctcgaaagcc tg           42

<210> SEQ ID NO 55
<211> LENGTH: 34
<212> TYPE: DNA
<213> ORGANISM: Artificial Sequence
<220> FEATURE:
<223> OTHER INFORMATION: Primer

<400> SEQUENCE: 55
agaaagctgg gttttaagcc caccaagcag ttgc                    34

<210> SEQ ID NO 56
<211> LENGTH: 30
<212> TYPE: DNA
<213> ORGANISM: Artificial Sequence
<220> FEATURE:
<223> OTHER INFORMATION: Primer
```

```
<400> SEQUENCE: 56
ggaattccat atgatggtga ggggcaaaac                                30

<210> SEQ ID NO 57
<211> LENGTH: 31
<212> TYPE: DNA
<213> ORGANISM: Artificial Sequence
<220> FEATURE:
<223> OTHER INFORMATION: Primer

<400> SEQUENCE: 57
cgggatcctc actttcttga agaacaaggt a                              31

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58
ggaattccat atgatggtga ggggcaaaac                                30

<210> SEQ ID NO 59
<211> LENGTH: 33
<212> TYPE: DNA
<213> ORGANISM: Artificial Sequence
<220> FEATURE:
<223> OTHER INFORMATION: Primer

<400> SEQUENCE: 59
ggaattccat atgaagaaag cctttgagct ctc                            33

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
gggaattcgt ttctgaagaa aatatgcagc                                30

<210> SEQ ID NO 61
<211> LENGTH: 29
<212> TYPE: DNA
<213> ORGANISM: Artificial Sequence
<220> FEATURE:
<223> OTHER INFORMATION: Primer

<400> SEQUENCE: 61
cgggatcccc actttcaga gagcttctc                                  29

<210> SEQ ID NO 62
<211> LENGTH: 29
<212> TYPE: DNA
<213> ORGANISM: Artificial Sequence
<220> FEATURE:
<223> OTHER INFORMATION: Primer

<400> SEQUENCE: 62
tcagcggccg cgatggtgag gggcaaaac                                 29

<210> SEQ ID NO 63
```

```
<211> LENGTH: 33
<212> TYPE: DNA
<213> ORGANISM: Artificial Sequence
<220> FEATURE:
<223> OTHER INFORMATION: Primer

<400> SEQUENCE: 63
tcagcggccg cgatgaagaa agcctttgag ctc                                    33

<210> SEQ ID NO 64
<211> LENGTH: 35
<212> TYPE: DNA
<213> ORGANISM: Artificial Sequence
<220> FEATURE:
<223> OTHER INFORMATION: Primer

<400> SEQUENCE: 64
tcagcggccg cgatggtttc tgaagaaaat atgca                                  35

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
gaagatcttc accactttc agagagcttc                                         30

<210> SEQ ID NO 66
<211> LENGTH: 31
<212> TYPE: DNA
<213> ORGANISM: Artificial Sequence
<220> FEATURE:
<223> OTHER INFORMATION: Primer

<400> SEQUENCE: 66
ccgctcgagg gatggtgagg ggcaaaactc a                                      31

<210> SEQ ID NO 67
<211> LENGTH: 34
<212> TYPE: DNA
<213> ORGANISM: Artificial Sequence
<220> FEATURE:
<223> OTHER INFORMATION: Primer

<400> SEQUENCE: 67
cgggatcctc actttcttga agaacaaggt aacc                                   34

<210> SEQ ID NO 68
<211> LENGTH: 34
<212> TYPE: DNA
<213> ORGANISM: Artificial Sequence
<220> FEATURE:
<223> OTHER INFORMATION: Primer

<400> SEQUENCE: 68
gcggatcccc ctttcttgaa gaacaaggta accc                                   34

<210> SEQ ID NO 69
<211> LENGTH: 30
<212> TYPE: DNA
<213> ORGANISM: Artificial Sequence
<220> FEATURE:
<223> OTHER INFORMATION: Primer

<400> SEQUENCE: 69
```
ccgctcgagc atggtgaggg gcaaaactca          30

<210> SEQ ID NO 70
<211> LENGTH: 34
<212> TYPE: DNA
<213> ORGANISM: Artificial Sequence
<220> FEATURE:
<223> OTHER INFORMATION: Primer

<400> SEQUENCE: 70
ccgctcgagc atgaagaaag cctttgagct ctca          34

<210> SEQ ID NO 71
<211> LENGTH: 34
<212> TYPE: DNA
<213> ORGANISM: Artificial Sequence
<220> FEATURE:
<223> OTHER INFORMATION: Primer

<400> SEQUENCE: 71
ccgctcgagc atggtttctg aagaaaatat gcag          34

<210> SEQ ID NO 72
<211> LENGTH: 34
<212> TYPE: DNA
<213> ORGANISM: Artificial Sequence
<220> FEATURE:
<223> OTHER INFORMATION: Primer

<400> SEQUENCE: 72
gcggatcccc cacttttcag agagcttctc gttt          34

<210> SEQ ID NO 73
<211> LENGTH: 29
<212> TYPE: DNA
<213> ORGANISM: Artificial Sequence
<220> FEATURE:
<223> OTHER INFORMATION: Primer

<400> SEQUENCE: 73
tcccccgggg atggtgaggg gcaaaactc          29

<210> SEQ ID NO 74
<211> LENGTH: 34
<212> TYPE: DNA
<213> ORGANISM: Artificial Sequence
<220> FEATURE:
<223> OTHER INFORMATION: Primer

<400> SEQUENCE: 74
tcccccgggt cactttcttg aagaacaagg taac          34

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
ggaggcacct caggtcattt          20

<210> SEQ ID NO 76
<211> LENGTH: 20
<212> TYPE: DNA

```
<213> ORGANISM: Artificial Sequence
<220> FEATURE:
<223> OTHER INFORMATION: Primer

<400> SEQUENCE: 76
atagcggtca ttgtcttgcg                                              20

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
tacgctggtg acctctgctc                                              20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
ggttctcctc ctcctcctcc                                              20

<210> SEQ ID NO 79
<211> LENGTH: 21
<212> TYPE: DNA
<213> ORGANISM: Artificial Sequence
<220> FEATURE:
<223> OTHER INFORMATION: Primer

<400> SEQUENCE: 79
aagagccttc gtagcatcag g                                            21

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
cgcaacgtca tctccttctg                                              20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
caagataaac cggcaggtga                                              20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
cccttggtgg agaagacgat                                              20
```

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
ttcgccaccg actcatgtat                                               20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
cgtgacacca gtttccctga                                               20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
gcaggaggag aacaaggctc                                               20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
ctgttcccac tgcacttgct                                               20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
gaagtgttgt cgaacgagcg                                               20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
ccattcctct gcttcttccc                                               20

<210> SEQ ID NO 89
<211> LENGTH: 20
<212> TYPE: DNA
<213> ORGANISM: Artificial Sequence
<220> FEATURE:

<223> OTHER INFORMATION: Primer

<400> SEQUENCE: 89
tacgacagct tcgacttcgc                                           20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
gggtggtgga gtaggttgct                                           20

<210> SEQ ID NO 91
<211> LENGTH: 32
<212> TYPE: DNA
<213> ORGANISM: Artificial Sequence
<220> FEATURE:
<223> OTHER INFORMATION: Primer

<400> SEQUENCE: 91
gctctagaat gcaggcaggc cggctcgatc gg                             32

<210> SEQ ID NO 92
<211> LENGTH: 32
<212> TYPE: DNA
<213> ORGANISM: Artificial Sequence
<220> FEATURE:
<223> OTHER INFORMATION: Primer

<400> SEQUENCE: 92
gcggatccga gagcgatttc tgccgggcag tc                             32

<210> SEQ ID NO 93
<211> LENGTH: 32
<212> TYPE: DNA
<213> ORGANISM: Artificial Sequence
<220> FEATURE:
<223> OTHER INFORMATION: Primer

<400> SEQUENCE: 93
gctctagaat ggtgcggggg aagacgcagc tg                             32

<210> SEQ ID NO 94
<211> LENGTH: 37
<212> TYPE: DNA
<213> ORGANISM: Artificial Sequence
<220> FEATURE:
<223> OTHER INFORMATION: Primer

<400> SEQUENCE: 94
gctctagaat gaaggcgcac gagctctccg tcctctg                        37

<210> SEQ ID NO 95
<211> LENGTH: 30
<212> TYPE: DNA
<213> ORGANISM: Artificial Sequence
<220> FEATURE:
<223> OTHER INFORMATION: Primer

<400> SEQUENCE: 95
gctctagaat gacggcacag caagacatag                                30

```
<210> SEQ ID NO 96
<211> LENGTH: 36
<212> TYPE: DNA
<213> ORGANISM: Artificial Sequence
<220> FEATURE:
<223> OTHER INFORMATION: Primer

<400> SEQUENCE: 96
gcggatccgc accttgcccc ttagatcttc gttctc                                 36

<210> SEQ ID NO 97
<211> LENGTH: 35
<212> TYPE: DNA
<213> ORGANISM: Artificial Sequence
<220> FEATURE:
<223> OTHER INFORMATION: Primer

<400> SEQUENCE: 97
cgcgcgatcg catgcaggca ggccggctcg atcgg                                  35

<210> SEQ ID NO 98
<211> LENGTH: 36
<212> TYPE: DNA
<213> ORGANISM: Artificial Sequence
<220> FEATURE:
<223> OTHER INFORMATION: Primer

<400> SEQUENCE: 98
tcgtttaaac tcaagagcga tttctgccgg gcagtc                                 36

<210> SEQ ID NO 99
<211> LENGTH: 38
<212> TYPE: DNA
<213> ORGANISM: Artificial Sequence
<220> FEATURE:
<223> OTHER INFORMATION: Primer

<400> SEQUENCE: 99
cgcgcgatcg catggtgcgg gggaagacgc agctgaag                               38

<210> SEQ ID NO 100
<211> LENGTH: 36
<212> TYPE: DNA
<213> ORGANISM: Artificial Sequence
<220> FEATURE:
<223> OTHER INFORMATION: Primer

<400> SEQUENCE: 100
cgcgcgatcg catgaaggcg cacgagctct ccgtcc                                 36

<210> SEQ ID NO 101
<211> LENGTH: 33
<212> TYPE: DNA
<213> ORGANISM: Artificial Sequence
<220> FEATURE:
<223> OTHER INFORMATION: Primer

<400> SEQUENCE: 101
cgcgcgatcg catgacggca cagcaagaca tag                                    33

<210> SEQ ID NO 102
<211> LENGTH: 38
<212> TYPE: DNA
<213> ORGANISM: Artificial Sequence
<220> FEATURE:
<223> OTHER INFORMATION: Primer
```

<400> SEQUENCE: 102
tcgtttaaac tcacaccttg ccccttagat cttcgttc                               38

<210> SEQ ID NO 103
<211> LENGTH: 43
<212> TYPE: DNA
<213> ORGANISM: Artificial Sequence
<220> FEATURE:
<223> OTHER INFORMATION: Primer

<400> SEQUENCE: 103
aaaaagcagg ctctatgcag gcaggccggc tcgatcggag agg                         43

<210> SEQ ID NO 104
<211> LENGTH: 52
<212> TYPE: DNA
<213> ORGANISM: Artificial Sequence
<220> FEATURE:
<223> OTHER INFORMATION: Primer

<400> SEQUENCE: 104
agaaagctgg gtttcaagag cgatttctgc cgggcagtcc gatgaacagc tc               52

<210> SEQ ID NO 105
<211> LENGTH: 44
<212> TYPE: DNA
<213> ORGANISM: Artificial Sequence
<220> FEATURE:
<223> OTHER INFORMATION: Primer

<400> SEQUENCE: 105
aaaaagcagg ctctatggtg cggggggaaga cgcagctgaa gcgg                       44

<210> SEQ ID NO 106
<211> LENGTH: 48
<212> TYPE: DNA
<213> ORGANISM: Artificial Sequence
<220> FEATURE:
<223> OTHER INFORMATION: Primer

<400> SEQUENCE: 106
agaaagctgg gtttcagctg gcgaactcgt agaggcggcc gctggggg                    48

<210> SEQ ID NO 107
<211> LENGTH: 44
<212> TYPE: DNA
<213> ORGANISM: Artificial Sequence
<220> FEATURE:
<223> OTHER INFORMATION: Primer

<400> SEQUENCE: 107
aaaaagcagg ctctatggtg cggggggaaga cgcagctgaa gcgg                       44

<210> SEQ ID NO 108
<211> LENGTH: 45
<212> TYPE: DNA
<213> ORGANISM: Artificial Sequence
<220> FEATURE:
<223> OTHER INFORMATION: Primer

<400> SEQUENCE: 108
aaaaagcagg ctctatgaag gcgcacgagc tctccgtcct ctgcg                       45

<210> SEQ ID NO 109
<211> LENGTH: 45

```
<212> TYPE: DNA
<213> ORGANISM: Artificial Sequence
<220> FEATURE:
<223> OTHER INFORMATION: Primer

<400> SEQUENCE: 109
aaaaagcagg ctctatgacg gcacagcaag acatagagaa gataa        45

<210> SEQ ID NO 110
<211> LENGTH: 47
<212> TYPE: DNA
<213> ORGANISM: Artificial Sequence
<220> FEATURE:
<223> OTHER INFORMATION: Primer

<400> SEQUENCE: 110
agaaagctgg gttttacacc ttgcccctta gatcttcgtt ctccttg      47

<210> SEQ ID NO 111
<211> LENGTH: 30
<212> TYPE: DNA
<213> ORGANISM: Artificial Sequence
<220> FEATURE:
<223> OTHER INFORMATION: Primer

<400> SEQUENCE: 111
cgggatccat gacggcacag caagacatag                         30

<210> SEQ ID NO 112
<211> LENGTH: 33
<212> TYPE: DNA
<213> ORGANISM: Artificial Sequence
<220> FEATURE:
<223> OTHER INFORMATION: Primer

<400> SEQUENCE: 112
ggaattcctt acaccttgcc ccttagatct tcg                     33

<210> SEQ ID NO 113
<211> LENGTH: 33
<212> TYPE: DNA
<213> ORGANISM: Artificial Sequence
<220> FEATURE:
<223> OTHER INFORMATION: Primer

<400> SEQUENCE: 113
tcgaattcta tgcaggcagg ccggctcgat cgg                     33

<210> SEQ ID NO 114
<211> LENGTH: 35
<212> TYPE: DNA
<213> ORGANISM: Artificial Sequence
<220> FEATURE:
<223> OTHER INFORMATION: Primer

<400> SEQUENCE: 114
ggtggatcct caagagcgat ttctgccggg cagtc                   35

<210> SEQ ID NO 115
<211> LENGTH: 39
<212> TYPE: DNA
<213> ORGANISM: Artificial Sequence
<220> FEATURE:
<223> OTHER INFORMATION: Primer

<400> SEQUENCE: 115
```

```
                                          -continued gctcaagctt cgatggtgcg ggggaagacg cagctgaag                              39

<210> SEQ ID NO 116
<211> LENGTH: 41
<212> TYPE: DNA
<213> ORGANISM: Artificial Sequence
<220> FEATURE:
<223> OTHER INFORMATION: Primer

<400> SEQUENCE: 116
gctcaagctt cgatgaaggc gcacgagctc tccgtcctct g                           41

<210> SEQ ID NO 117
<211> LENGTH: 42
<212> TYPE: DNA
<213> ORGANISM: Artificial Sequence
<220> FEATURE:
<223> OTHER INFORMATION: Primer

<400> SEQUENCE: 117
gctcaagctt cgatgacggc acagcaagac atagagaaga ta                          42

<210> SEQ ID NO 118
<211> LENGTH: 43
<212> TYPE: DNA
<213> ORGANISM: Artificial Sequence
<220> FEATURE:
<223> OTHER INFORMATION: Primer

<400> SEQUENCE: 118
cgcggtacct tacaccttgc cccttagatc ttcgttctcc ttg                         43
```